(12) United States Patent
Cesarini et al.

(10) Patent No.: US 7,510,563 B2
(45) Date of Patent: Mar. 31, 2009

(54) RECIPROCATING ROTARY ARTHROSCOPIC SURGICAL INSTRUMENT

(75) Inventors: Peter M Cesarini, Londonderry, NH (US); Karen Drucker, Danville, NH (US); Rafal Jezierski, Boston, MA (US); Roger R. Cassidy, Jr., Methuen, MA (US)

(73) Assignee: Smith & Nephew, Inc., Memphis, TN (US)

(*) Notice: Subject to any disclaimer, the term of this patent is extended or adjusted under 35 U.S.C. 154(b) by 495 days.

(21) Appl. No.: 10/318,400

(22) Filed: Dec. 13, 2002

(65) Prior Publication Data

US 2004/0092980 A1 May 13, 2004

Related U.S. Application Data

(63) Continuation of application No. PCT/US02/34128, filed on Oct. 25, 2002, which is a continuation-in-part of application No. 09/983,810, filed on Oct. 26, 2001, now Pat. No. 7,226,459.

(51) Int. Cl.
*A61B 17/32* (2006.01)
*A61B 10/00* (2006.01)
(52) U.S. Cl. ............... 606/170; 606/180; 600/566
(58) Field of Classification Search ........... 606/159, 606/169, 170, 180, 185, 107, 83, 171; 600/566, 600/567; 408/129; 81/33; D8/59; 604/22; 175/317; 166/377
See application file for complete search history.

(56) References Cited

U.S. PATENT DOCUMENTS

| | | | | |
|---|---|---|---|---|
| 1,585,934 A | * | 5/1926 | Muir | 600/567 |
| 1,785,086 A | * | 12/1930 | Hauk | 175/317 |
| 2,708,437 A | * | 5/1955 | Hutchins | 606/171 |
| 3,995,619 A | * | 12/1976 | Glatzer | 600/567 |
| 4,316,465 A | * | 2/1982 | Dotson, Jr. | 604/22 |
| 4,493,698 A | | 1/1985 | Wang et al. | |
| 4,517,977 A | | 5/1985 | Frost | |
| 4,649,919 A | | 3/1987 | Thimsen et al. | |
| 4,867,157 A | | 9/1989 | McGurk-Burleson et al. | |
| 4,940,061 A | | 7/1990 | Terwilliger et al. | |
| 5,007,917 A | | 4/1991 | Evans | |
| 5,106,364 A | | 4/1992 | Hayafuji et al. | |
| 5,116,868 A | | 5/1992 | Chen et al. | |
| 5,152,744 A | | 10/1992 | Krause et al. | |
| 5,176,677 A | | 1/1993 | Wuchinich | |
| 5,269,785 A | | 12/1993 | Bonutti | |

(Continued)

OTHER PUBLICATIONS

International Search Report, PCT/US 02/34128 mailed Jan. 30, 2003.

(Continued)

*Primary Examiner*—Julian W Woo
(74) *Attorney, Agent, or Firm*—Norman F. Hainer, Jr.

(57) ABSTRACT

A surgical instrument includes a cutting member with an implement for cutting tissue, and a drive coupled to the cutting member. The drive may include a drive member having a helical groove and being attached to the cutting member. Furthermore, the drive may include an inner drive hub coupled to the drive member such that the drive member rotates with the inner drive hub while being free to translate relative to the inner drive hub. The drive simultaneously rotates and translates the cutting member in response to a force applied to the drive.

48 Claims, 24 Drawing Sheets

U.S. PATENT DOCUMENTS

| | | |
|---|---|---|
| 5,304,118 A | 4/1994 | Trese et al. |
| 5,312,425 A | 5/1994 | Evans et al. |
| 5,364,395 A * | 11/1994 | West, Jr. ............ 606/170 |
| 5,395,313 A | 3/1995 | Naves et al. |
| 5,409,013 A | 4/1995 | Clement |
| 5,425,376 A | 6/1995 | Banys et al. |
| 5,429,601 A | 7/1995 | Conley et al. |
| 5,456,689 A | 10/1995 | Kresch et al. |
| 5,490,860 A | 2/1996 | Middle et al. |
| 5,569,284 A | 10/1996 | Young et al. |
| 5,591,187 A | 1/1997 | Dekel |
| 5,649,547 A | 7/1997 | Ritchart et al. |
| 5,702,420 A | 12/1997 | Sterling et al. |
| 5,741,286 A | 4/1998 | Recuset |
| 5,741,287 A | 4/1998 | Alden et al. |
| 5,857,995 A | 1/1999 | Thomas et al. |
| 5,873,886 A | 2/1999 | Larsen et al. |
| 5,911,699 A | 6/1999 | Anis et al. |
| 5,913,867 A | 6/1999 | Dion |
| 5,925,055 A | 7/1999 | Adrian et al. |
| 5,928,163 A * | 7/1999 | Roberts et al. ............ 600/567 |
| 6,004,320 A | 12/1999 | Casscells et al. |
| 6,007,513 A | 12/1999 | Anis et al. |
| 6,068,641 A | 5/2000 | Varsseveld |
| 6,120,147 A | 9/2000 | Vijfvinkel et al. |
| 6,132,448 A | 10/2000 | Perez et al. |
| 6,203,518 B1 | 3/2001 | Anis et al. |
| 6,217,543 B1 | 4/2001 | Anis et al. |
| 6,224,603 B1 | 5/2001 | Marino |
| 6,258,111 B1 | 7/2001 | Ross et al. |
| 6,277,096 B1 | 8/2001 | Cortella et al. |
| 6,474,418 B2 * | 11/2002 | Miramon ............ 166/377 |
| 6,656,132 B1 | 12/2003 | Ouchi |
| 6,712,773 B1 | 3/2004 | Viola |
| 2003/0078609 A1 | 4/2003 | Finlay et al. |

OTHER PUBLICATIONS

Fishing Reel produced and sold by Shimano of Japan into the U.S. prior to Oct. 26, 2001, 7 pages.

* cited by examiner

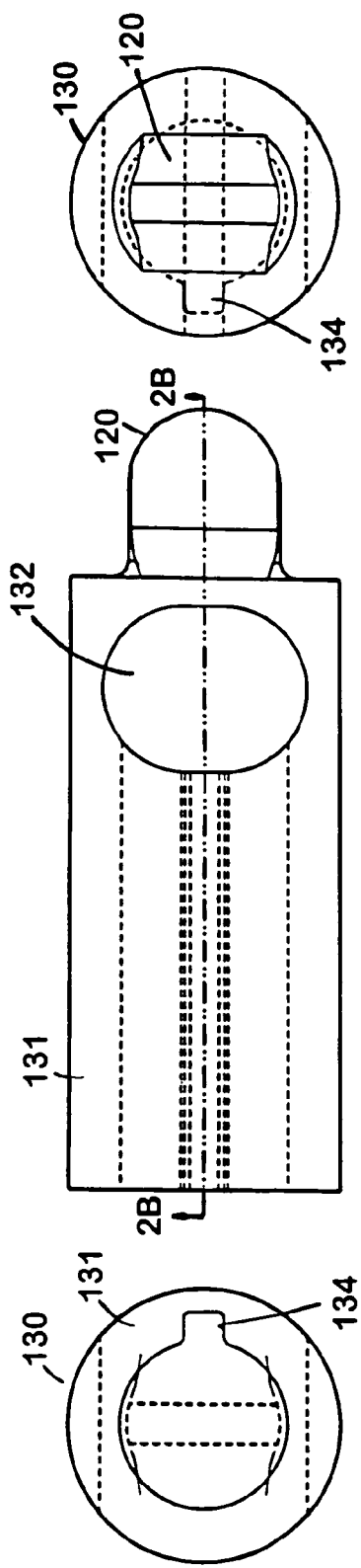
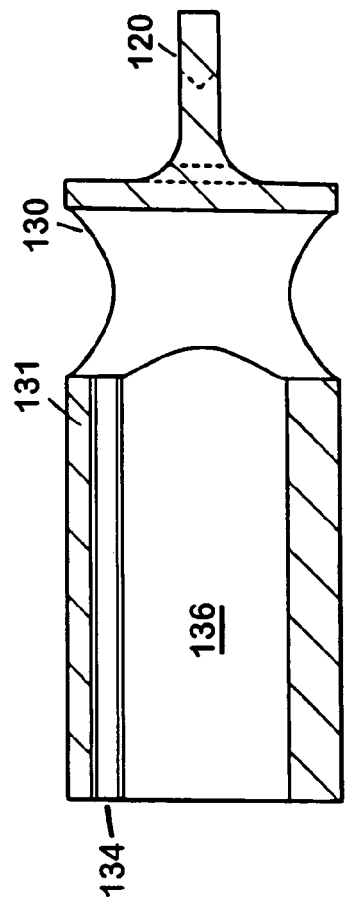
Fig. 2D
Fig. 2A
Fig. 2C
Fig. 2B

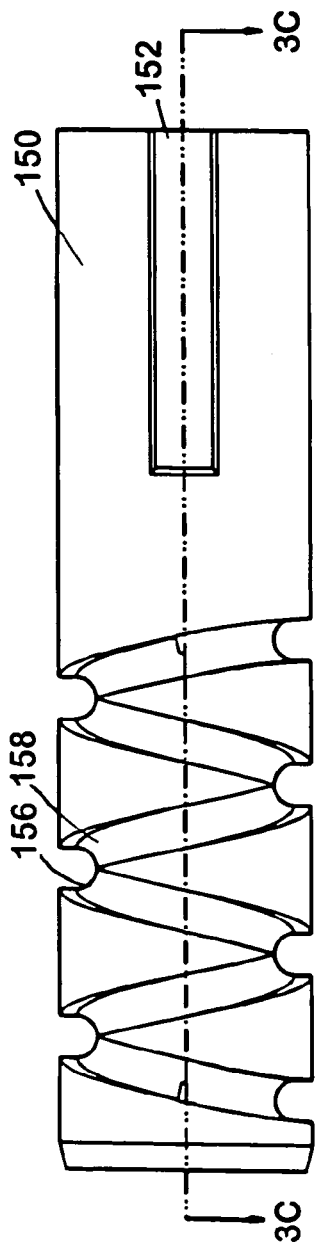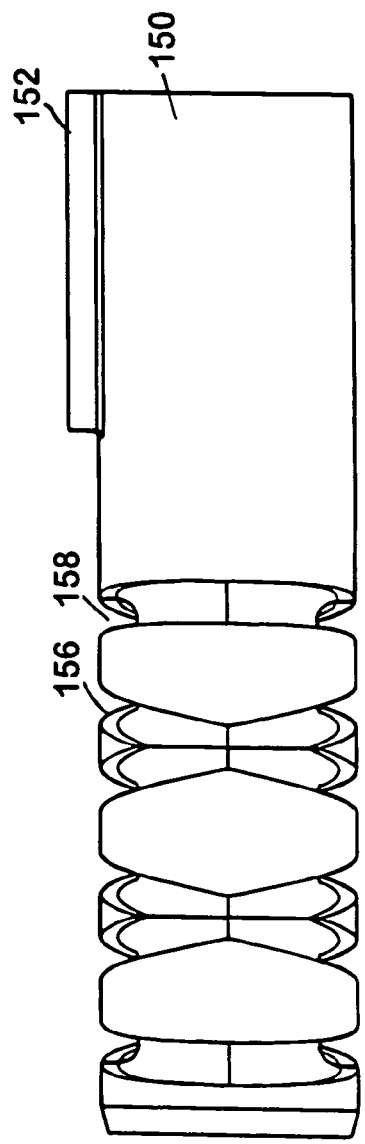
Fig. 3A
Fig. 3B

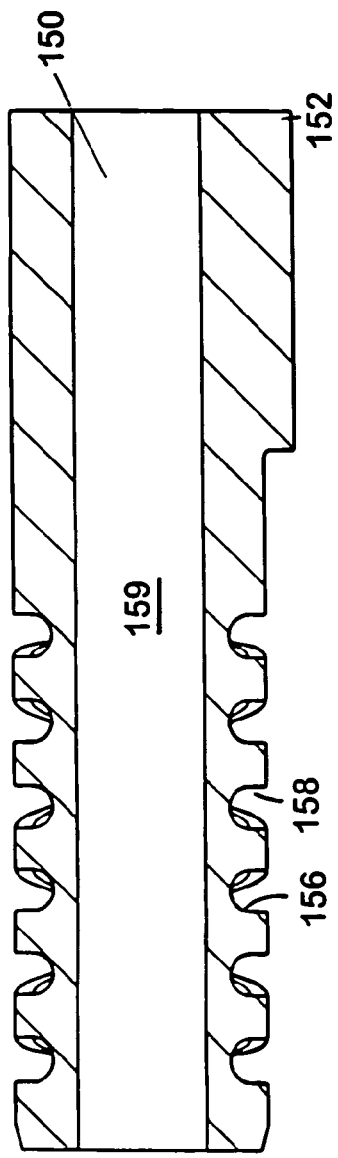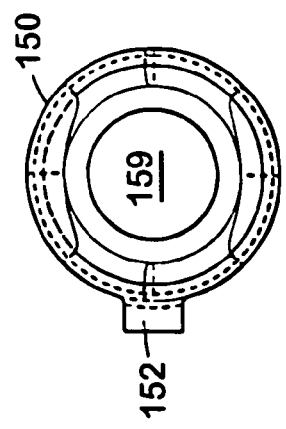
Fig. 3C
Fig. 3D

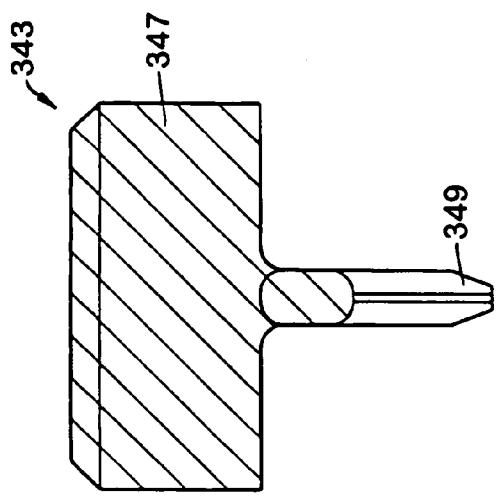
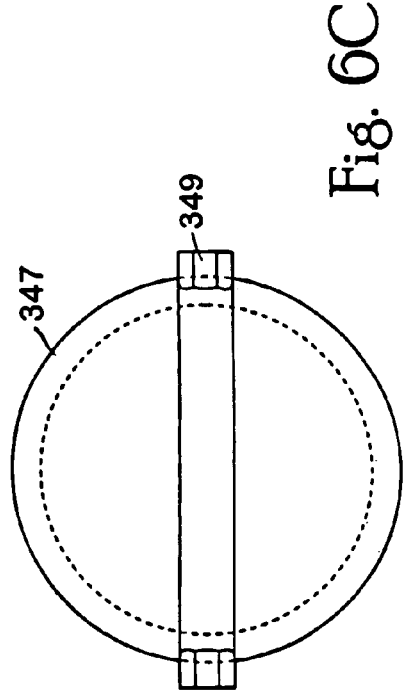
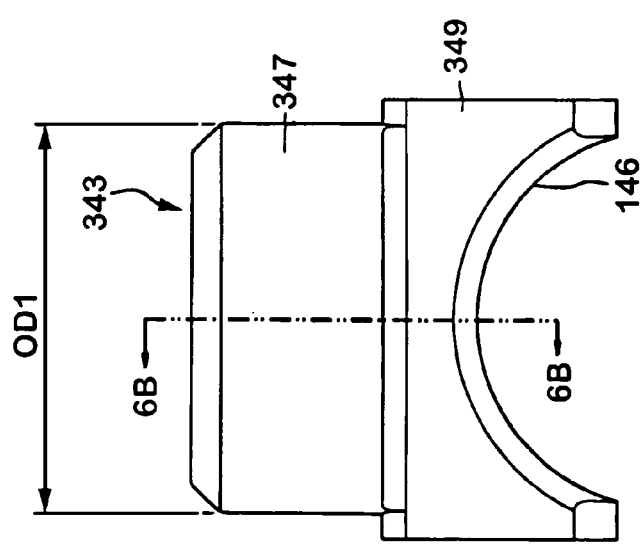
Fig. 6B
Fig. 6C
Fig. 6A

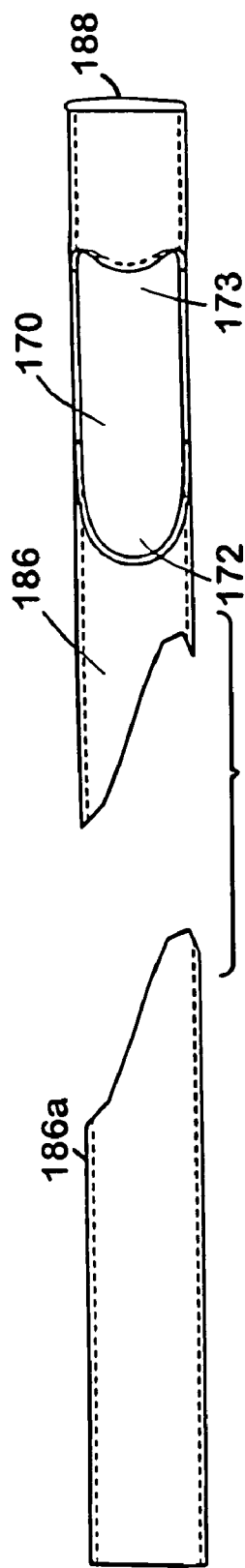
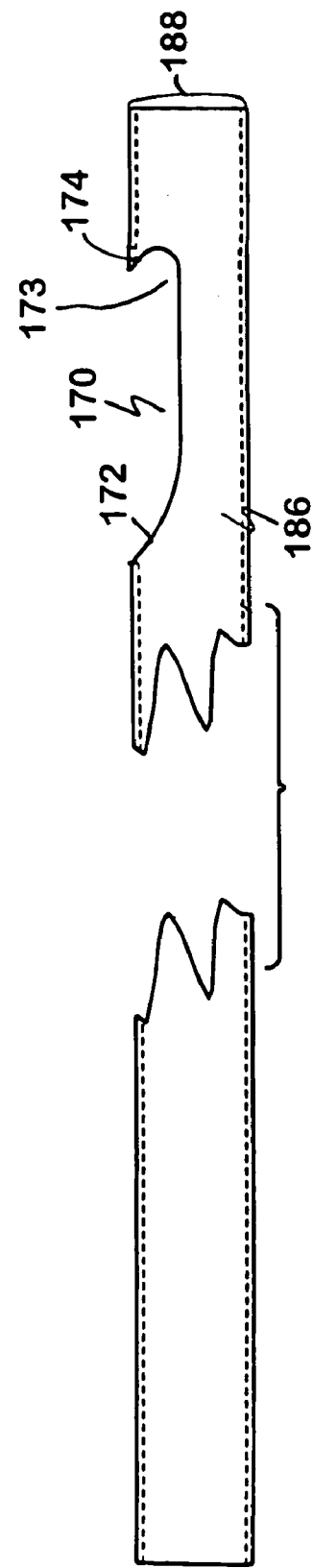
Fig. 8A
Fig. 8B

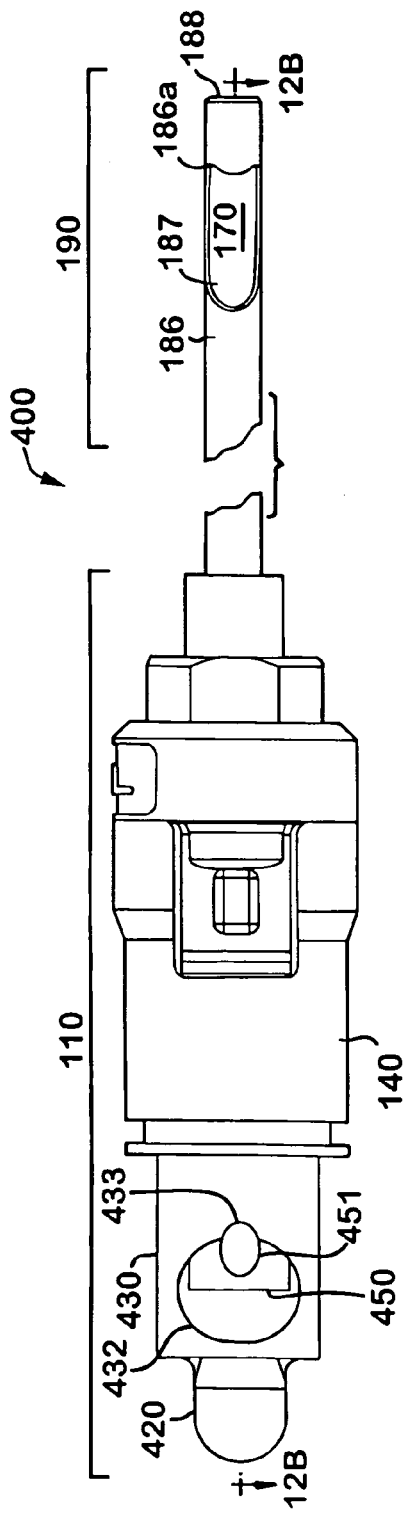
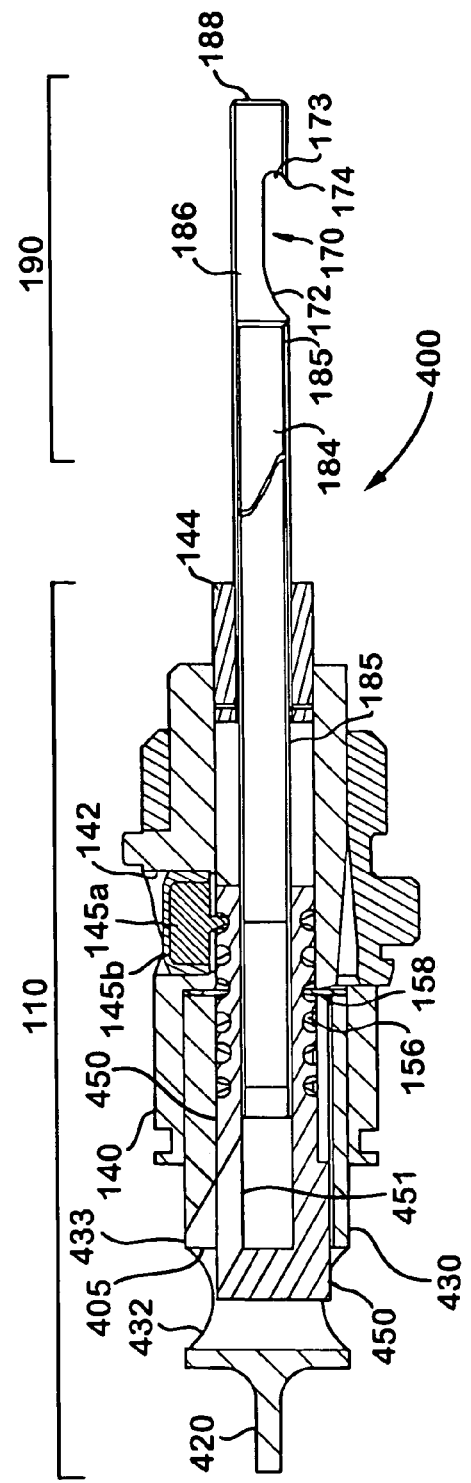
Fig. 12A
Fig. 12B

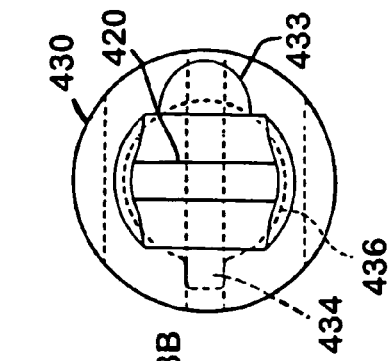
Fig. 13D
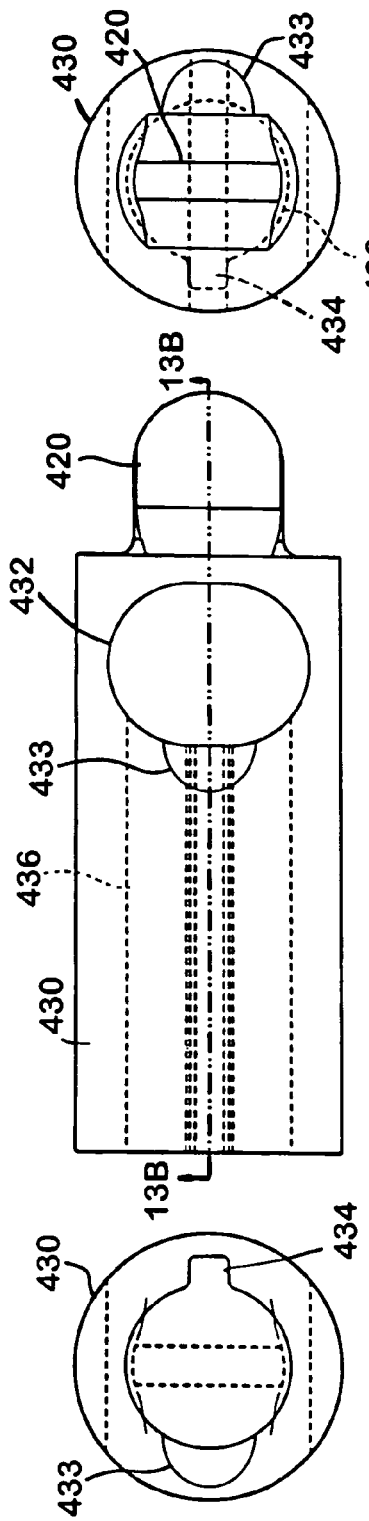
Fig. 13A
Fig. 13C
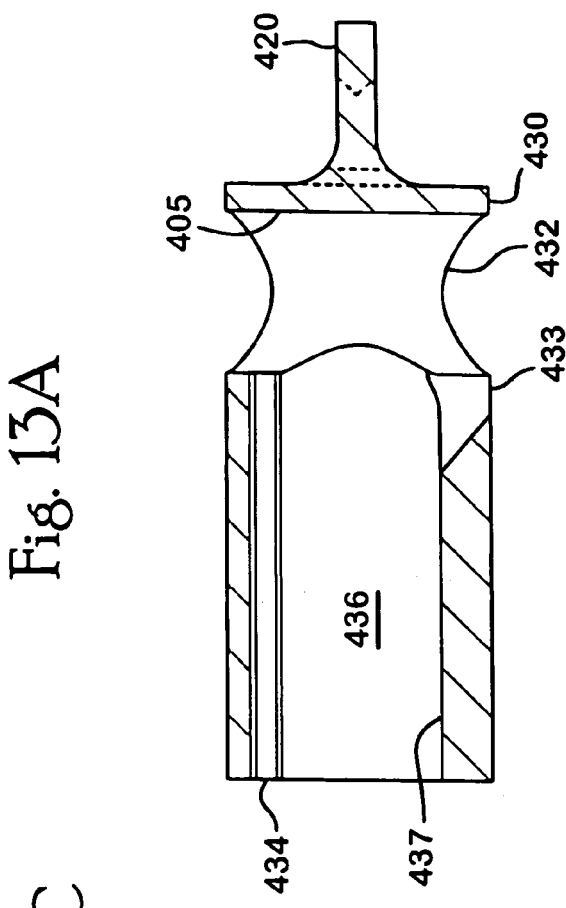
Fig. 13B

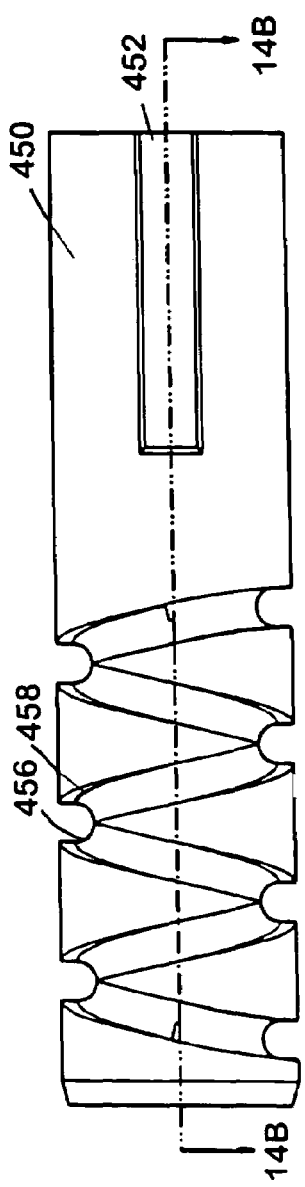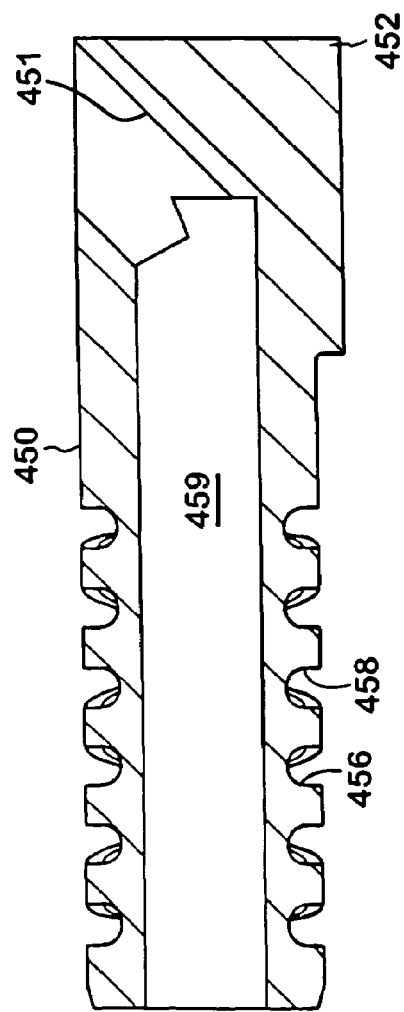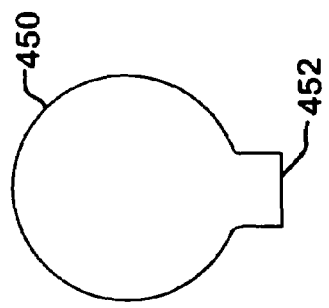
Fig. 14A
Fig. 14B
Fig. 14C

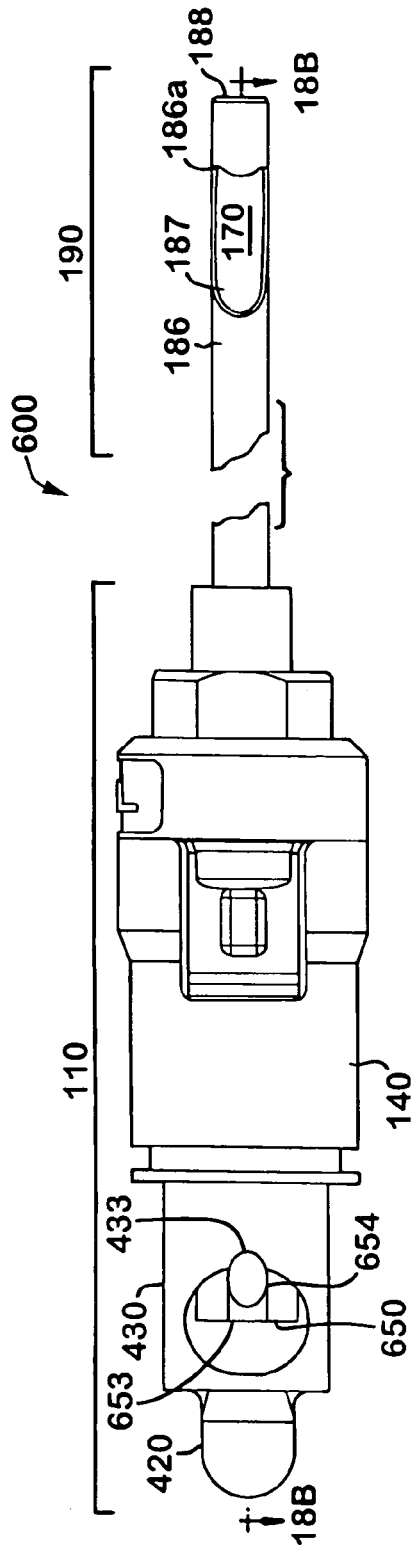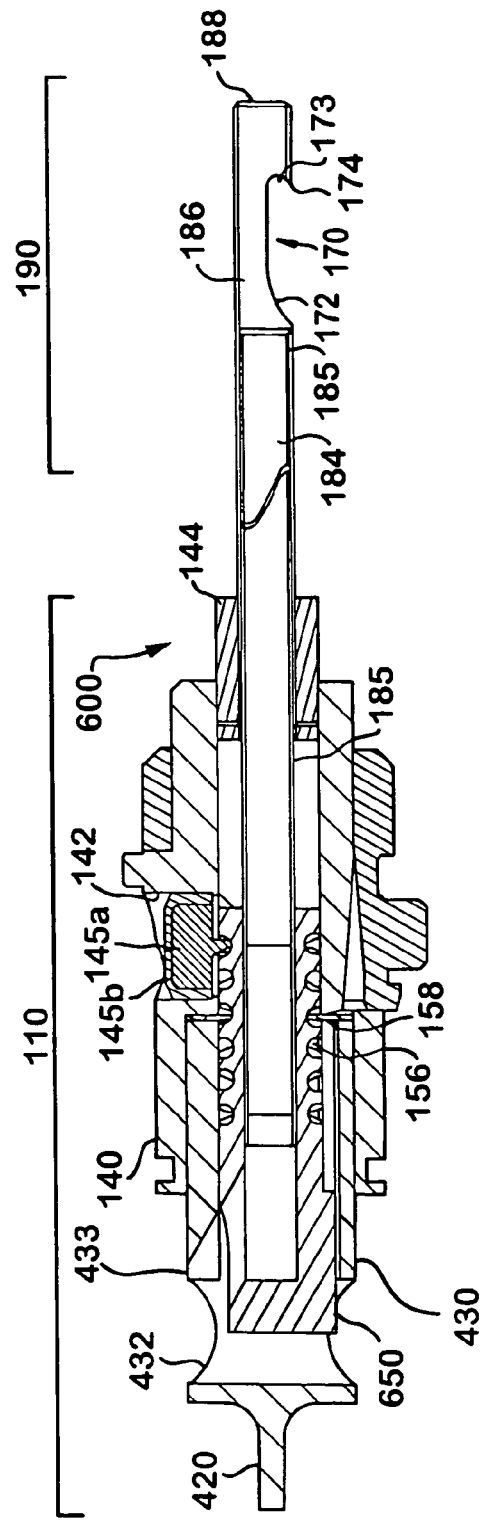

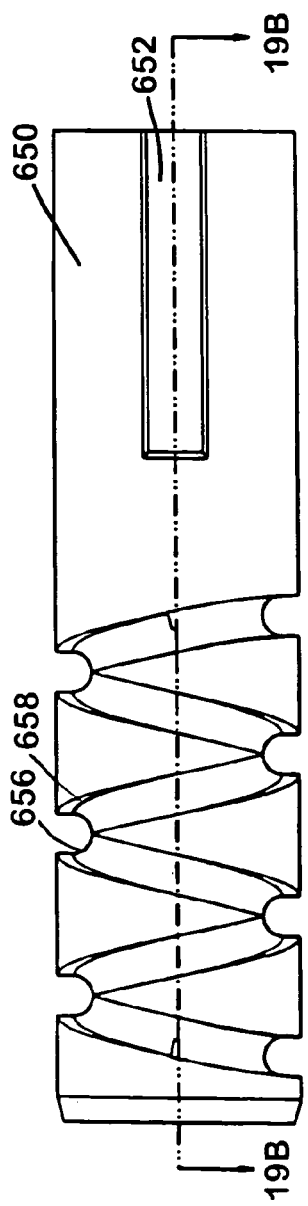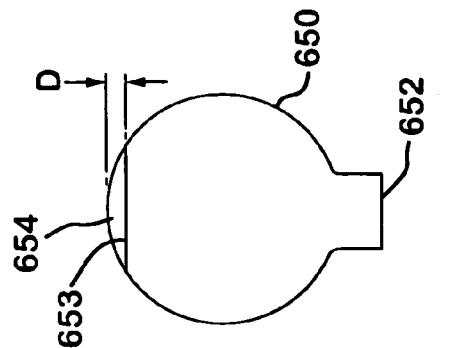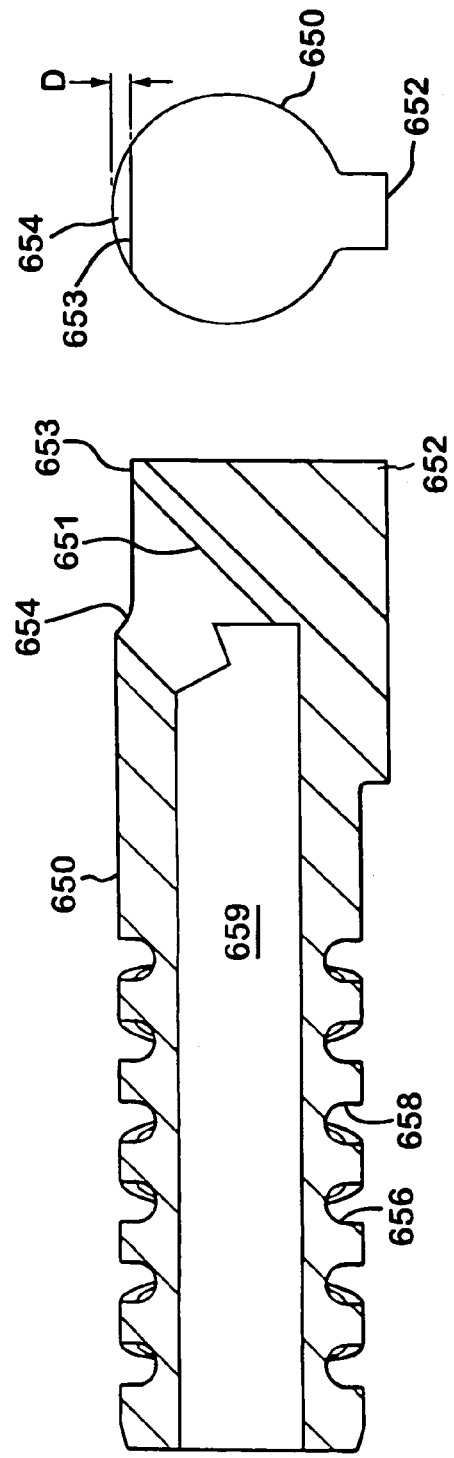
Fig. 19A
Fig. 19C
Fig. 19B

RECIPROCATING ROTARY ARTHROSCOPIC SURGICAL INSTRUMENT

CROSS REFERENCE TO RELATED APPLICATIONS

This application is a continuation of and claims the benefit of priority of Application No. PCT/US02/34128, filed Oct. 25, 2002, which is a continuation-in-part of and claims the benefit of priority of U.S. application Ser. No. 09/983,810, filed Oct. 26, 2001, now U.S. Pat. No. 7,226,459, the disclosures of which are considered part of (and are incorporated by reference in) the disclosure of this application.

TECHNICAL FIELD

This description relates to rotary cutting surgical instruments, and more particularly, to a reciprocating rotary surgical instrument for cutting tissue.

BACKGROUND

Conventional arthroscopic surgical instruments generally include an outer tube and a cutting member that rotates or translates axially within the outer tube. The outer tube and cutting member may interact to create shear forces that cut tissue. This type of cutting is generally used to cut soft tissue, such as muscle, ligaments, and tendons.

SUMMARY

In one aspect, a surgical instrument includes a cutting member with an implement for cutting tissue, and a drive coupled to the cutting member to simultaneously rotate and translate the cutting member in response to a force applied to the drive.

One or more of the following features may be included in the surgical instrument. For example, the drive may be configured such that the cutting member reciprocates. The drive may include a drive member attached to the cutting member and including a helical groove. The drive also may include a translation piece disposed in the groove such that rotary driving of the drive member results in simultaneous reciprocation of the drive member relative to the translation piece.

The drive also may include an inner drive hub coupled to the drive member. The inner drive hub defines a slot and the drive member includes a key received in the slot to rotary couple the drive member to the inner drive hub such that the drive member rotates with the inner drive hub while being free to translate relative to the inner drive hub. The helical groove may include a left-hand threaded helical channel and/or a right-hand threaded helical channel. The cutting member may be attached to the drive member to move rotatably and axially with the member.

The implement may include a chamfered cutting edge at a distal end of the cutting member. The chamfered edge may be a straight cutting edge. Alternatively, the chamfered edge may be an angled cutting edge.

The instrument may include an outer tubular member. The cutting member may be received within the outer member. The outer member may include a cutting window disposed proximate to a tip of the outer member. The cutting window may be an opening in the outer member exposing the cutting member to tissue. The cutting window may have a U-shaped proximal end and a saddle-shaped distal end that may include a hook.

The translation piece may include a follower received within the groove and a sealing cap over the follower. The follower may be free to swivel relative to the sealing cap. The follower may have an arched bridge shape. The translation piece may be coupled to the drive member such that the translation piece is disposed in the helical groove and swivels to follow the helical groove as the drive member rotates.

In another aspect, cutting tissue includes positioning an outer member such that tissue is located within the outer member, engaging the tissue with a cutting member received within the outer member, and simultaneously rotating and translating the cutting member to grasp and slice the tissue.

One or more of the following features may be included. For example, the translating may be reciprocating.

The cutting member may include a cutting window at a proximal end and a lumen extending from and communicating with the cutting window. The drive may include an aspiration opening. The instrument may also include a restriction mechanism that restricts fluid flow from the lumen to the aspiration opening when the cutting window is open.

In another aspect, cutting tissue includes providing a surgical instrument having an outer member and a cutting member received within the outer member for movement relative to the outer member, and applying a slicing cutting motion to the tissue with the cutting member to mechanically cut the tissue.

In another aspect, cutting tissue includes applying a slicing cutting motion to tissue with a member, and mechanically driving the member to undergo simultaneous rotation and translation. The translation may include reciprocation.

The cutting edge of conventional arthroscopic surgical instruments, such as rotary shears, may have difficulty initiating a cut into semi-rigid tissue and may tend to bounce away from the tissue. Toothed edge geometry somewhat ameliorates this problem because the teeth attempt to pierce the tissue to initiate a cut. However, the efficiency of using teeth is limited and the limitations are more evident when cutting large volumes of semi-rigid tissue, such as meniscus or intrauterine fibroid tissue. The simultaneous rotating and translating cutting member of the surgical instrument overcomes these difficulties. The grasping of the tissue limits the tendency of the instrument to bounce away from the tissue when the tissue is being sliced. In particular, the instrument and method provide a higher resection rate to shorten procedure length, during, for example, fibroid and polyp resection.

Efficiency of conventional surgical instruments is also affected by operative cavity pressure and the need to clear blood and tissue fragments. The opening in the helical member of the surgical instrument, oriented at an angle relative to the lumen of the helical member, facilitates tissue evacuation, minimizes clogging of the instrument, and maintains operative cavity pressure. In particular, the opening provides for a pulsed fluid flow through the opening.

In another aspect, cutting tissue includes pulsing fluid through a cutting window and a lumen of a cutting member to remove cut tissue. The pulsing includes restricting fluid flow from the lumen of the cutting member to an aspiration opening proximal to the lumen when the cutting window is open. The pulsing may include permitting fluid to flow from the lumen of the cutting member to the aspiration opening when the cutting window is closed.

In a further aspect, cutting tissue includes coupling first and second openings in a surgical instrument during a cutting cycle to pulse fluid through a lumen of a drive member to remove fluid from the surgical instrument. The first and second openings are decoupled in the surgical instrument during the cutting cycle to prevent fluid from flowing from the surgical instrument when the openings are decoupled.

The openings in the inner hub and the helical member create a pulse flow action that reduces clogs within the instrument, permits use of lower vacuum settings for the instrument, and enables improved control over operative cavity pressure. Additionally, the inner hub and helical member openings facilitate clearance of blood and tissue fragments from the operative cavity and improve visualization of the operative cavity. Furthermore, because fluid is pulsed from the instrument, fluid may be conserved during the operation.

The details of one or more implementations are set forth in the accompanying drawings and the description below. Other features will be apparent from the description and drawings, and from the claims.

DESCRIPTION OF DRAWINGS

FIG. 2A is a top view of the inner drive hub of the surgical instrument of FIG. 1A.

FIG. 2B is a cross-sectional view taken along section 2B-2B of FIG. 2A.

FIGS. 2C and 2D are, respectively, distal and proximal end views of the inner drive hub of the surgical instrument of FIG. 1A.

FIGS. 3A and 3B are, respectively, top and side views of the helical member of the surgical instrument of FIG. 1A.

FIG. 3C is a cross-sectional view taken along section 3C-3C of FIG. 3A.

FIG. 3D is a proximal end view of the helical member of the surgical instrument of FIG. 1A.

FIG. 6A is a side view of the follower of the translation piece of the surgical instrument of FIG. 1A.

FIG. 6B is a cross-sectional view taken along section 6B-6B of FIG. 6A.

FIG. 6C is a top view of the follower of the translation piece of the surgical instrument of FIG. 1A.

FIGS. 8A and 8B are, respectively, top and side views of the outer member of the surgical instrument of FIG. 1A.

FIG. 12A is a side view of a reciprocating rotary surgical instrument.

FIG. 12B is a cross-sectional view taken along section 12B-12B of FIG. 12A.

FIG. 13A is a top view of the inner drive hub of the surgical instrument of FIG. 12A.

FIG. 13B is a cross-sectional view taken along section 13B-13B of FIG. 13A.

FIGS. 13C and 13D are, respectively, distal and proximal end views of the inner drive hub of the surgical instrument of FIG. 12A.

FIG. 14A is a top view of the helical member of the surgical instrument of FIG. 12A.

FIG. 14B is a cross-sectional view taken along section 14B-14B of FIG. 14A.

FIG. 14C is a proximal end view of the helical member of the surgical instrument of FIG. 12A.

FIG. 18A is a side view of a reciprocating rotary surgical instrument.

FIG. 18B is a cross-sectional view taken along section 18B-18B of FIG. 18A.

FIG. 19A is a top view of the helical member of the surgical instrument of FIG. 18A.

FIG. 19B is a cross-sectional view taken along section 19B-19B of FIG. 19A.

FIG. 19C is a proximal end view of the helical member of the surgical instrument of FIG. 18A.

Like reference symbols in the various drawings indicate like elements.

DETAILED DESCRIPTION

Figure 1A:
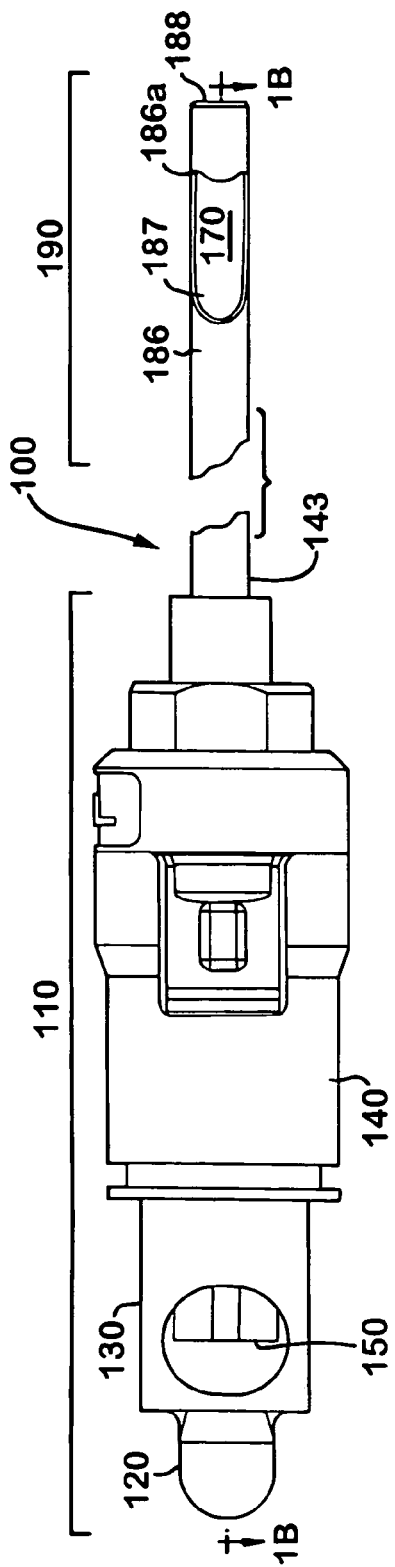
FIG. 1A is a side view of a reciprocating rotary surgical instrument.
Figure 1B:
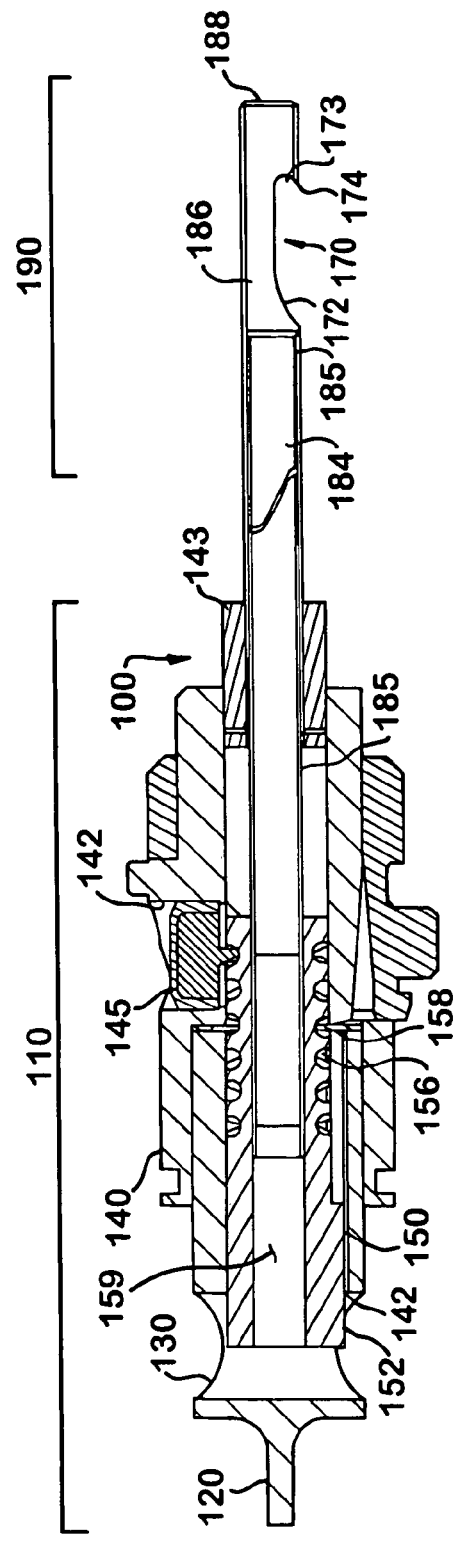
FIG. 1B is a cross-sectional view taken along section 1B-1B of FIG. 1A.

As shown in FIGS. 1A and 1B, a surgical instrument 100 includes a driving end 110 and a cutting end 190. The driving end 110 is located at the proximal end of the surgical instrument 100. The cutting end 190 is located at the distal end of the surgical instrument 100.

At the driving end 110, the instrument 100 includes a drive coupler 120 connected to an inner drive hub 130 that is positioned within an outer hub 140. The drive coupler 120 engages with a rotary driver (not shown) that turns the drive coupler 120 and causes the inner drive hub 130 to rotate. In one implementation, the rotary driver is a Dyonics Power Handpiece, No. 7205355, available from Smith & Nephew, Inc. of Andover, Mass. The inner drive hub 130 with the drive coupler 120 may be, for example, a component of Smith & Nephew disposable arthroscopic surgical instrument, No. 7205306, which is also available from Smith & Nephew, Inc. The instrument 100 includes a helical member 150 that rotates with the inner drive hub 130 in the outer hub 140. The helical member 150 and a translation piece 145 secured to the outer hub 140 are coupled together such that rotation of the helical member 150 causes linear translation of the helical member 150 relative to the outer hub 140, as described further below.

Figure 9:
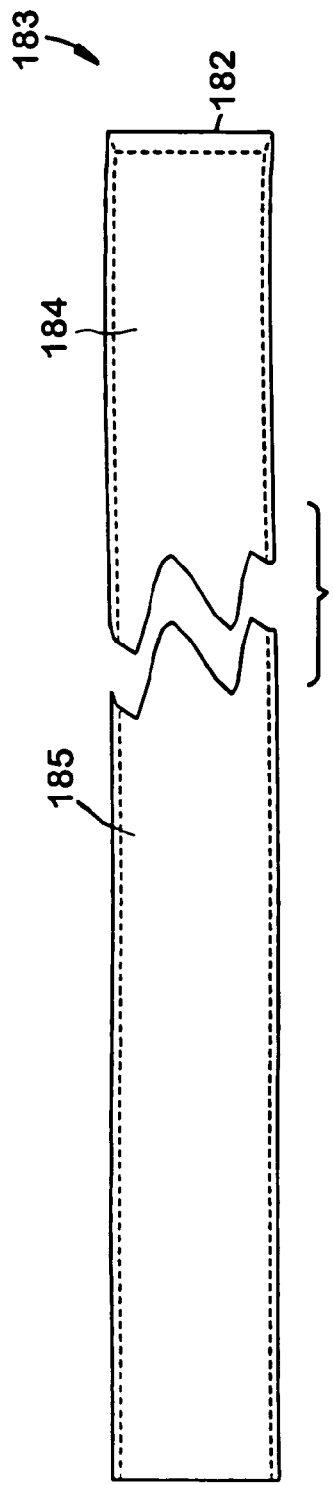
FIG. 9 is a side view of the cutting member of the surgical instrument of FIG. 1A.

The instrument 100 includes an elongated cutting member 185 and an elongated outer member 186. Referring also to FIG. 9, the cutting member 185 is generally tubular with a hollow interior 184. The distal end 183 of the cutting member 185 is chamfered to a sharp edge 182 for cutting. The cutting member 185 is fixed to the helical member 150 for axial and rotary motion therewith. The cutting member 185 is made of a suitable rigid material such as, for example, a metal alloy or plastic.

The outer member 186 is also tubular with a hollow interior 187. The cutting member 185 is received inside the outer member 186. The outer member 186 is disposed within the outer hub 140 and does not move relative to the outer hub 140. The outer member 186 is fixed to the outer hub 140 by a coupling 143 using, for example, epoxy, glue, insert molding, or spin-welding. The outer member 186 includes a blunt tip 188 having rounded corners. At the cutting end 190, the outer member 186 defines a cutting window 170 through a wall 186a of the outer member 186. The outer member 186 is made of a suitable rigid material such as, for example, a metal alloy or plastic.

Referring to FIGS. 2A-2D, the inner drive hub 130 includes the drive coupler 120, a lumen 136, an aspiration opening 132, and a slot 134. The drive coupler 120 extends from the proximal end of the inner drive hub 130 and mounts in the rotary driver. When the surgical instrument 100 is connected to the rotary driver, the aspiration opening 132 communicates with a suction mechanism coupled to the rotary driver. The slot 134 is disposed in a wall 131 of the inner drive hub 130. The slot 134 is like a track along one side of the inner drive hub 130. The slot 134 of the inner drive hub 130 is coupled with a key 152 of the helical member 150 (see FIG. 4B) so that rotation of the inner drive hub 130 causes the helical member 150 to rotate while allowing the helical member 150 to move axially relative to the inner drive hub 130, for example, the key 152 axially slides along the slot 134.

Referring to FIGS. 3A-3D, the helical member 150 of the surgical instrument 100 is formed of a lubricious material in a tubular shape with a through lumen 159. The cutting member 185 is disposed within the helical member 150 and fixed therein. The cutting member 185 may be secured using, for example, epoxy, injection-molding, or over-molded plastic. The hollow interior 184 of the cutting member 185 couples to the lumen 159 of the helical member 150, which communicates with the aspiration opening 132 in varying degrees during a reciprocating cycle. Accordingly, when the surgical instrument 100 is connected to the rotary driver, debris from the cutting end 190 of the surgical instrument 100 are aspirated through the hollow interior 184, the lumen 159, and the aspiration opening 132.

The helical member 150 includes the key 152 and two helical channels 156 and 158 disposed thereon. As shown in FIG. 3B, the key 152 is shaped like a fin and is located at the proximal end of the helical member 150. The key 152 mates with the slot 134 of the inner drive hub 130.

The two helical channels 156 and 158 are disposed on a distal portion of the exterior surface of the helical member 150. One helical channel 156 is right-hand threaded and the other helical channel 158 is left-hand threaded. As illustrated, the helical channels 156 and 158 have the same pitch (that is, the channels extend around the member 150 the same number of times). Other implementations may include helical channels with different pitches.

The length of the distal portion of the helical member 150 that includes the helical channels 156 and 158 is longer than the length of the cutting window 170. The helical channels 156 and 158 are smoothly blended together at their ends to form a continuous path or groove so that there is a smooth transition from one helical channel to the other helical channel at each end of the distal portion of the helical member 150.

Figure 4C:
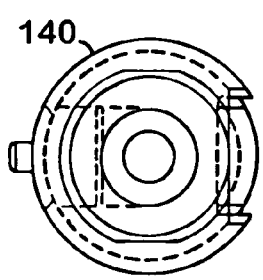
FIG. 4C is a distal end view of the outer hub of the surgical instrument of FIG. 1A.
Figure 4A:
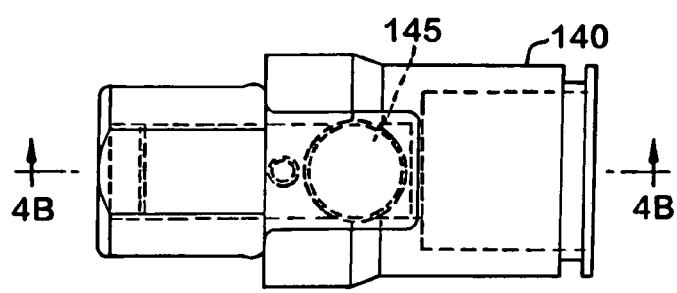
FIG. 4A is a top view of the outer hub of the surgical instrument of FIG. 1A.
Figure 4B:
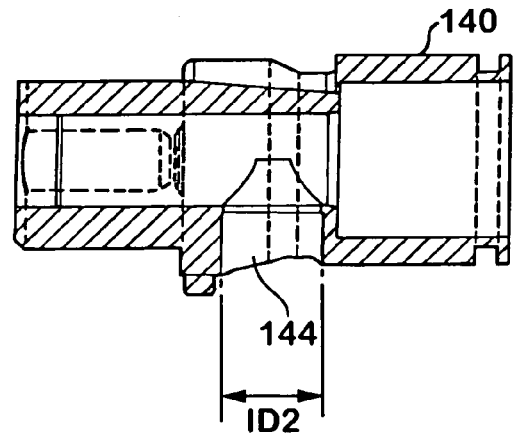
FIG. 4B is a cross-sectional view taken along section 4B-4B of FIG. 4A.

Referring to FIGS. 4A-4C, the outer hub 140 of the surgical instrument 100 is formed of hard plastic and does not move relative to the outer member 186. An example of an outer hub is a component of Smith & Nephew disposable arthroscopic surgical instrument, No. 7205306, modified with a cutout 144 for receiving the translation piece 145. The cutout 144 is disposed within a wall of the outer hub 140, for example, centrally, as in FIG. 4B, and aligned with the helical member. The translation piece 145 is located in the cutout 144 of the outer hub 140.

Referring to FIGS. 5A, 6A-6C, 7A, and 7B, the translation piece 145 includes a follower 343 and a cap 345. The follower 343 includes a cylindrical head 347 and two legs 349 protruding from the cylindrical head 347. The cylindrical head 347 has an outer diameter OD1 slightly less than an inner diameter ID1 of the cap 345. In this way, the cylindrical head 347 fits snugly within the cap 345. Also, the follower 343 is able to swivel or rotate because the cap 345 is a separate piece from the follower 343. The cap 345 has an outer diameter OD2 slightly less than an inner diameter ID2 of the cutout 144 to enable the piece 145 to fit within the cutout 144. In particular, the cap 345 covers the follower 343 and a seal is formed between the cap 345 and the cutout 144 to facilitate removal or suction of aspirated debris by the suction mechanism.

Figure 5A:
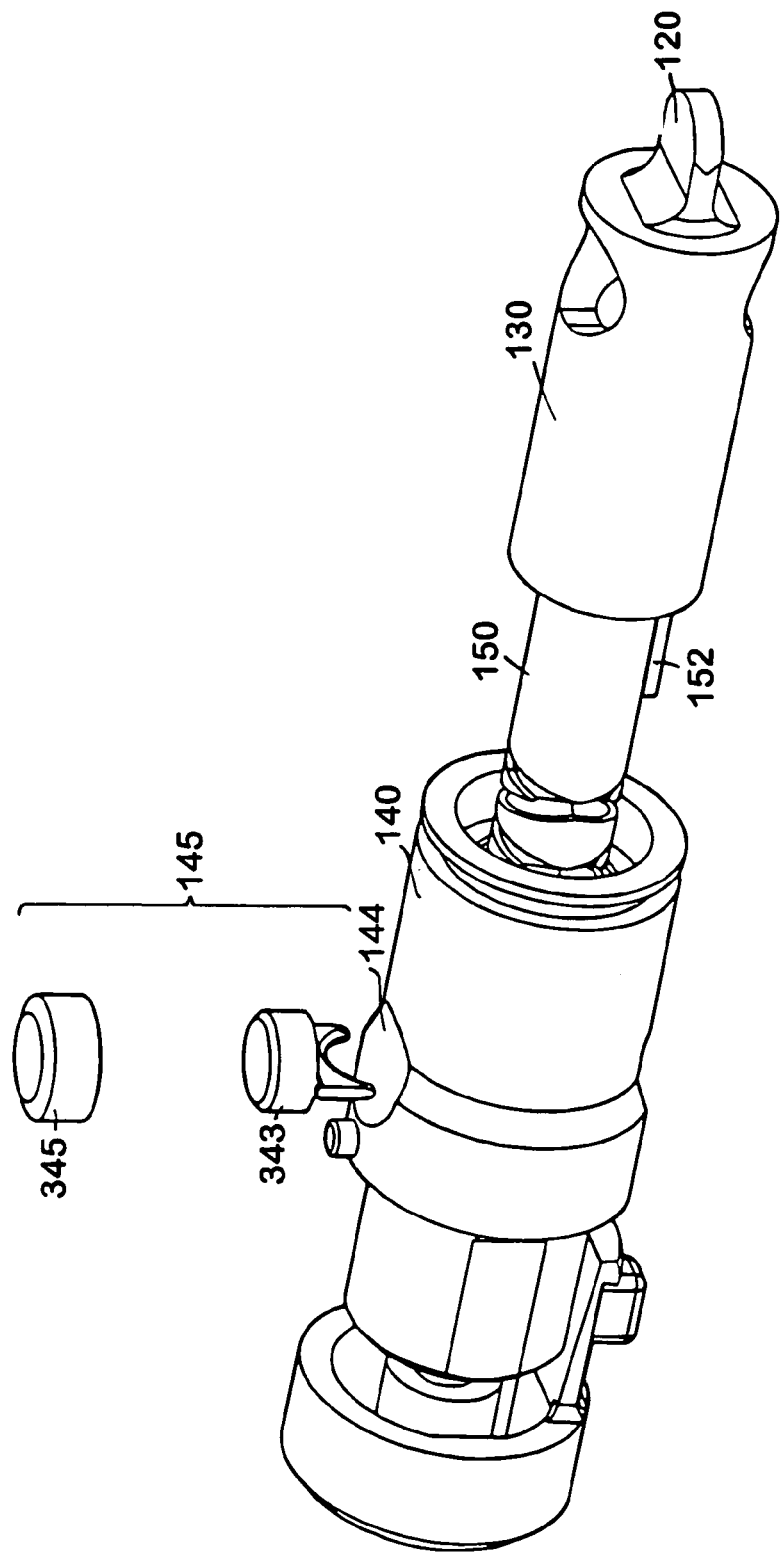
FIG. 5A is an exploded view of the translation piece and the helical member of the surgical instrument of FIG. 1A.
Figure 5B:
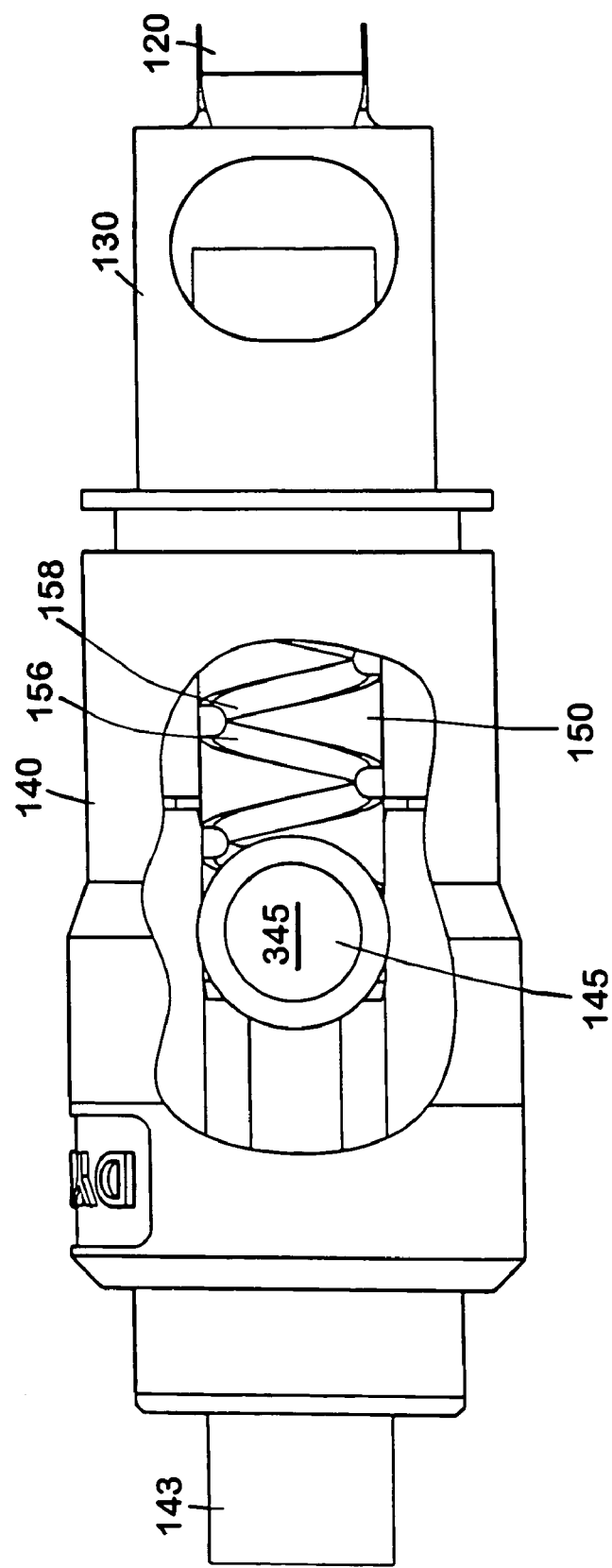
FIG. 5B is a partial cutaway view of the translation piece and the helical member of the surgical instrument of FIG. 1A.
Figure 5C:
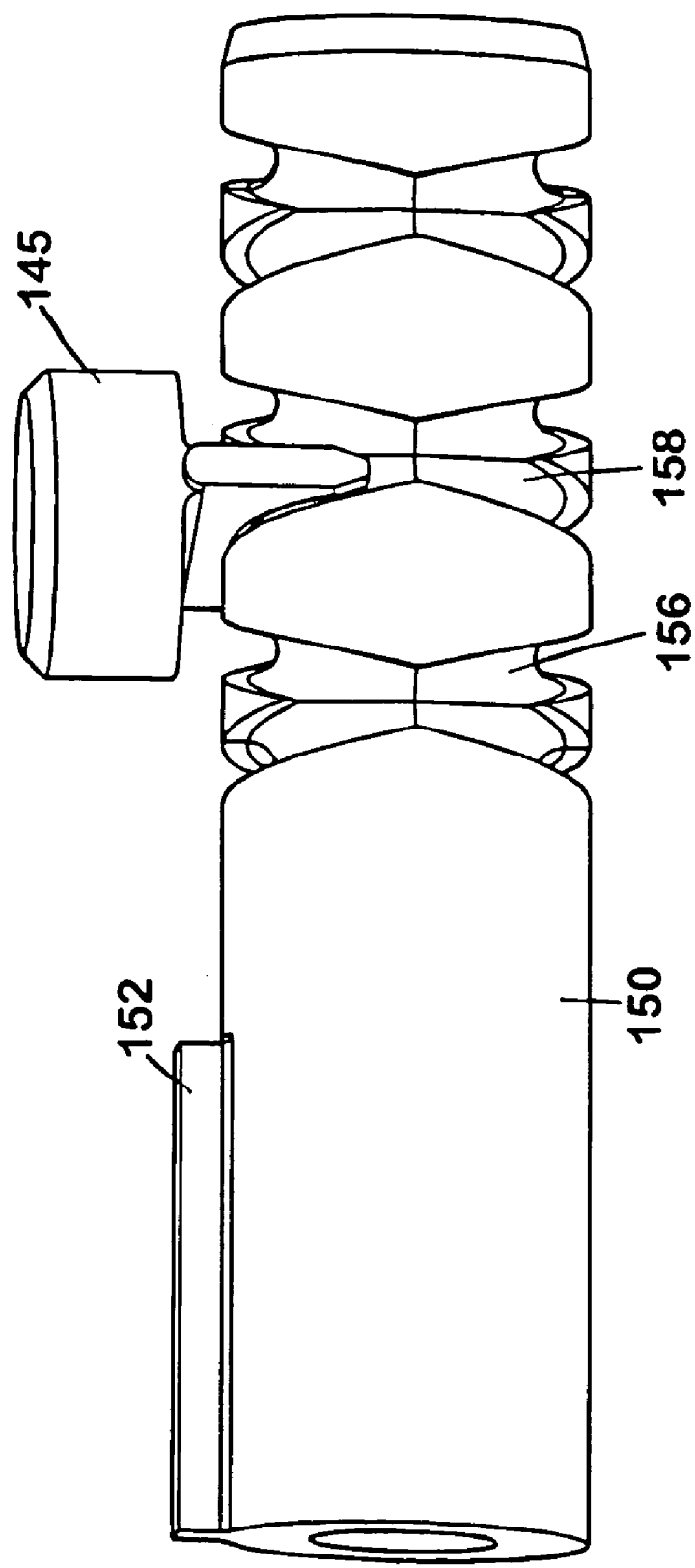
FIGS. 5C and 5D are side views of the translation piece and the helical member of the surgical instrument of FIG. 1A.
Figure 5D:
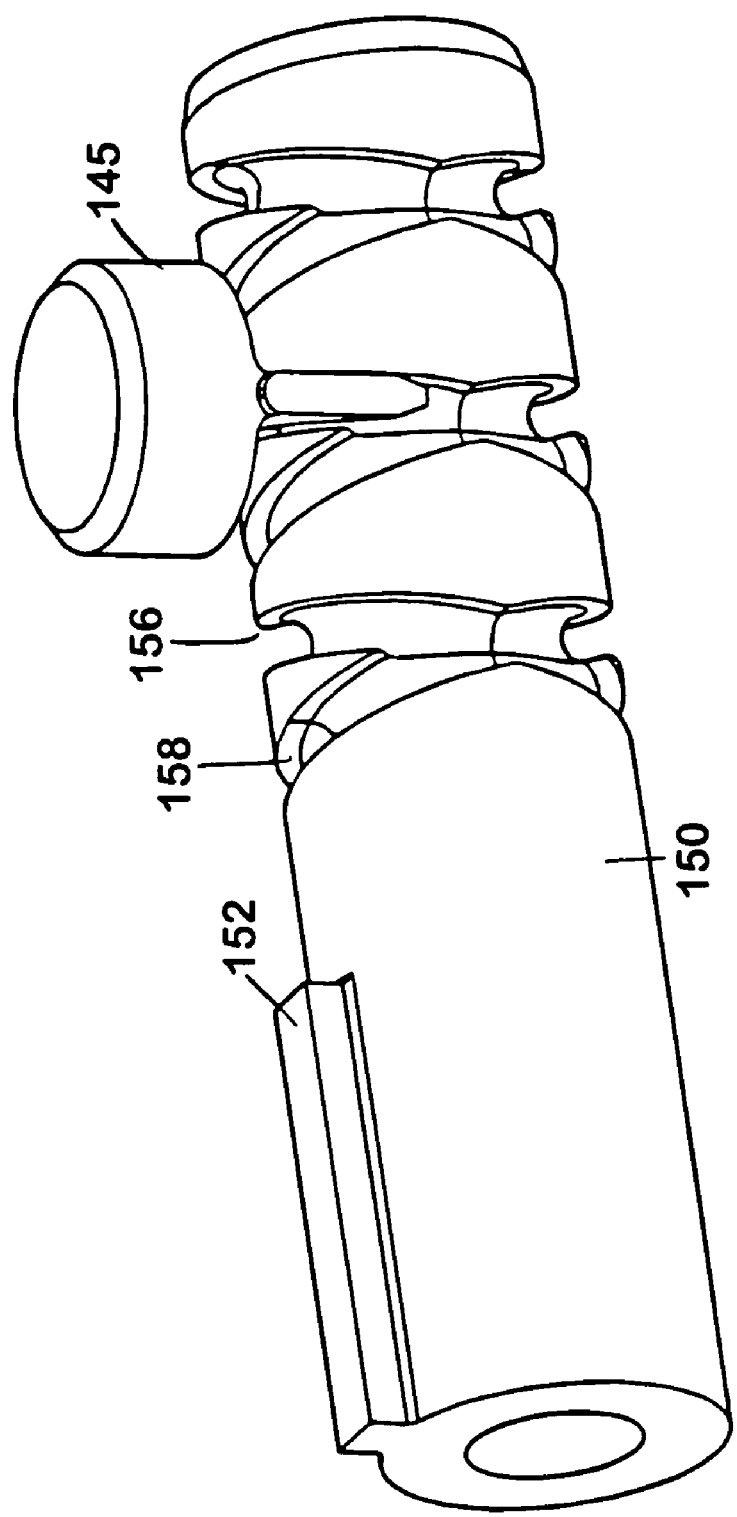
Figure 7A:
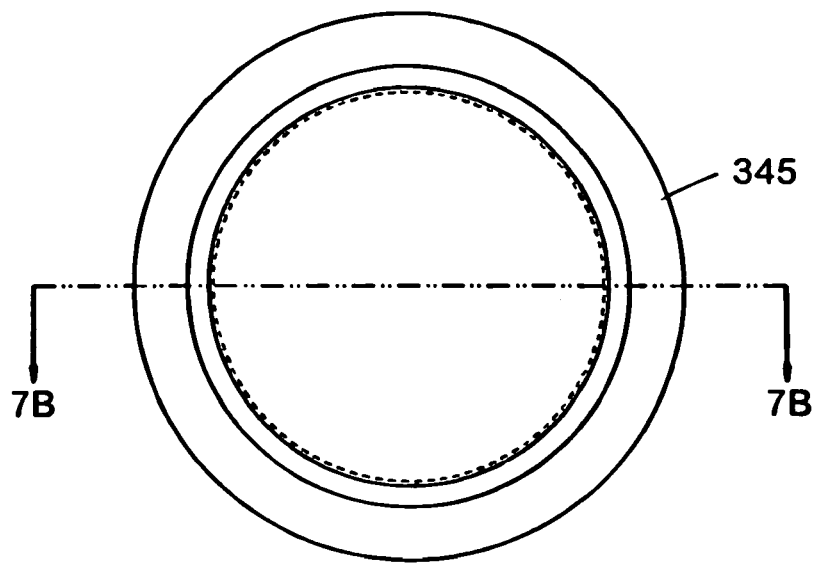
FIG. 7A is a top view of the cap for the follower of the translation piece of the surgical instrument of FIG. 1A.
Figure 7B:
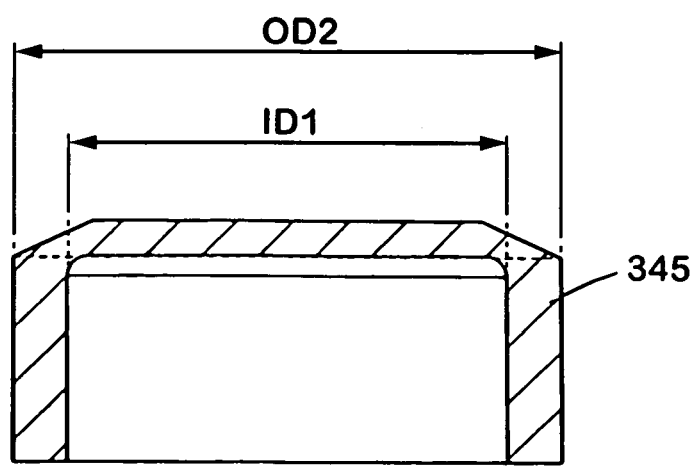
FIG. 7B is a cross-sectional view taken along section 7B-7B of FIG. 7A.

Referring to FIGS. 5B-5D, the legs 349 are sized to fit within the two helical channels 156 and 158 formed in the portion of the exterior surface of the helical member 150. The legs 349 form an arc 146 having a diameter that is sized to fit a diameter described by the helical channels 156 and 158 of the helical member 150.

Referring to FIGS. 8A and 8B, the outer member cutting window 170 has a generally oblong shape. The proximal end 172 of the cutting window 170 is U-shaped and the distal end 173 has a saddle shape that forms a hook 174. The distal end 173 is chamfered to provide a sharp edge 182. The cutting window 170 is disposed proximate to the tip 188 of the outer member 186. The cutting window 170 exposes the cutting member 185 over a length L.

In operation, the inner drive hub 130 is mechanically driven by the rotary driver that is engaged with the drive coupler 120. As inner drive hub 130 rotates, the helical member 150, which is coupled to the inner drive hub 130, rotates. As the helical member 150 rotates, the helical channels 156 and 158 rotate. If the follower 343 is not resting within either of the helical channels 156 and 158, then the rotary driver imparts only the rotational motion to the helical member 150. If, however, the follower 343 (in particular, the legs 349) is resting, for example, within the helical channel 156, then the rotary driver imparts an axial motion to the helical member 150. In particular, the legs 349 of the follower 343 follow the helical channel 156 as the helical channel 156 is rotating, and thereby impart an axial force on the edge of the helical channel 156. The imparted axial force causes the helical member 150 to translate axially.

As the follower 343 reaches one end of the helical channel 156, the follower 343 naturally swivels and smoothly transitions from the helical channel 156 to the helical channel 158.

Thus, the interaction between the follower 343 and the helical channel 156 causes the helical member 150 to move in a first axial direction until the follower 343 reaches the end of the helical channel 156, at which point the follower 343 swivels into the helical channel 158 and the helical member 150 moves in a second opposite axial direction. This back and forth axial motion is referred to as reciprocating motion. Furthermore, the drive coupler 120 of the inner drive hub 130 only needs to rotate in one direction and does not need to reverse rotational direction upon the translation piece 145 reaching the end of one of the helical channels 156 and 158. The cutting member 185, which is fixed to the helical member 150, simultaneously rotates about its longitudinal axis and reciprocates as the drive coupler 120 is driven by the rotary driver. In one implementation, a rate of the reciprocation cycle of the surgical instrument 100 may be 100 cycles per minute at 800 revolutions per minute (rpm).

Figure 10:
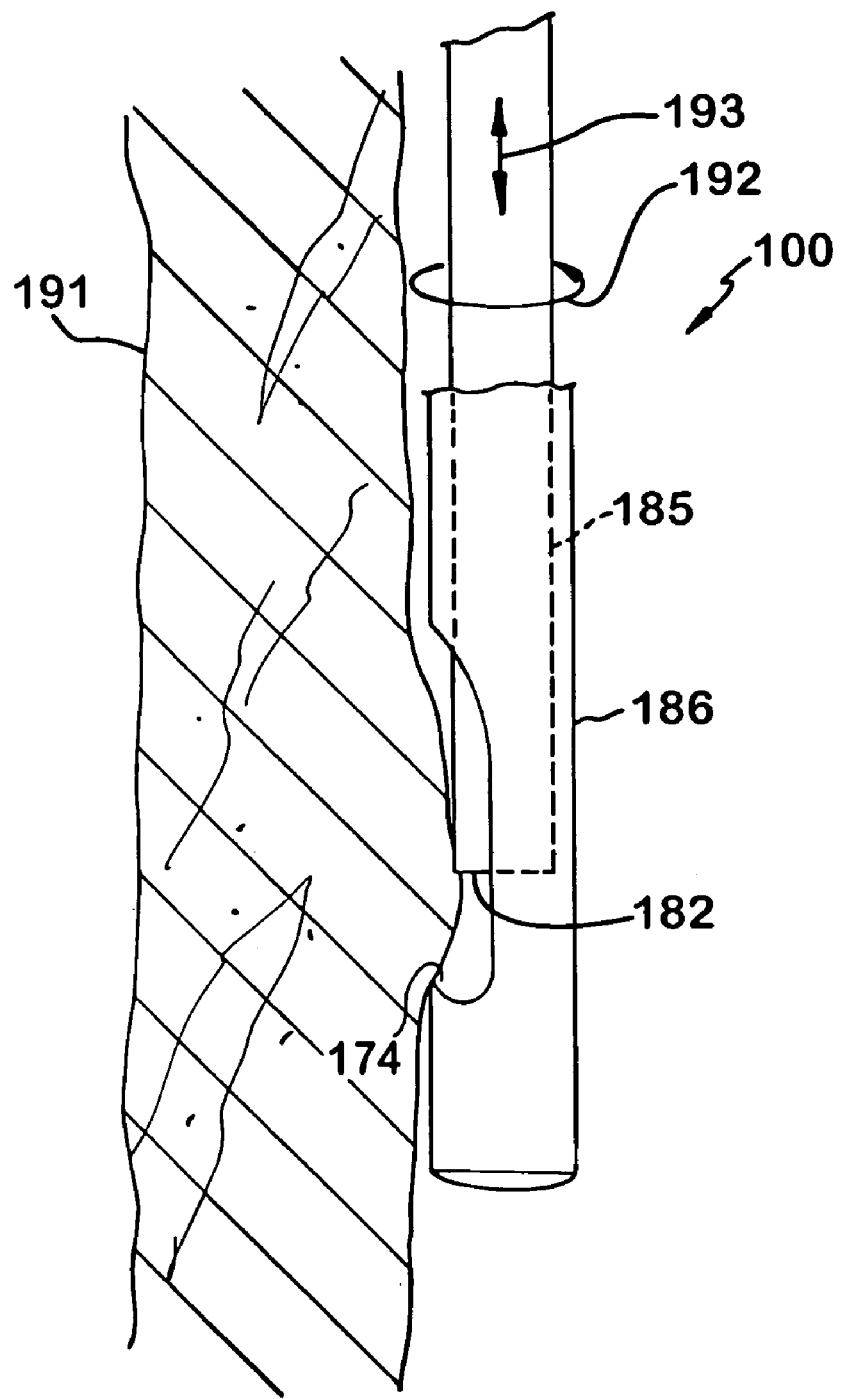
FIG. 10 illustrates the surgical instrument of FIG. 1A in use to cut tissue.
Figure 15:
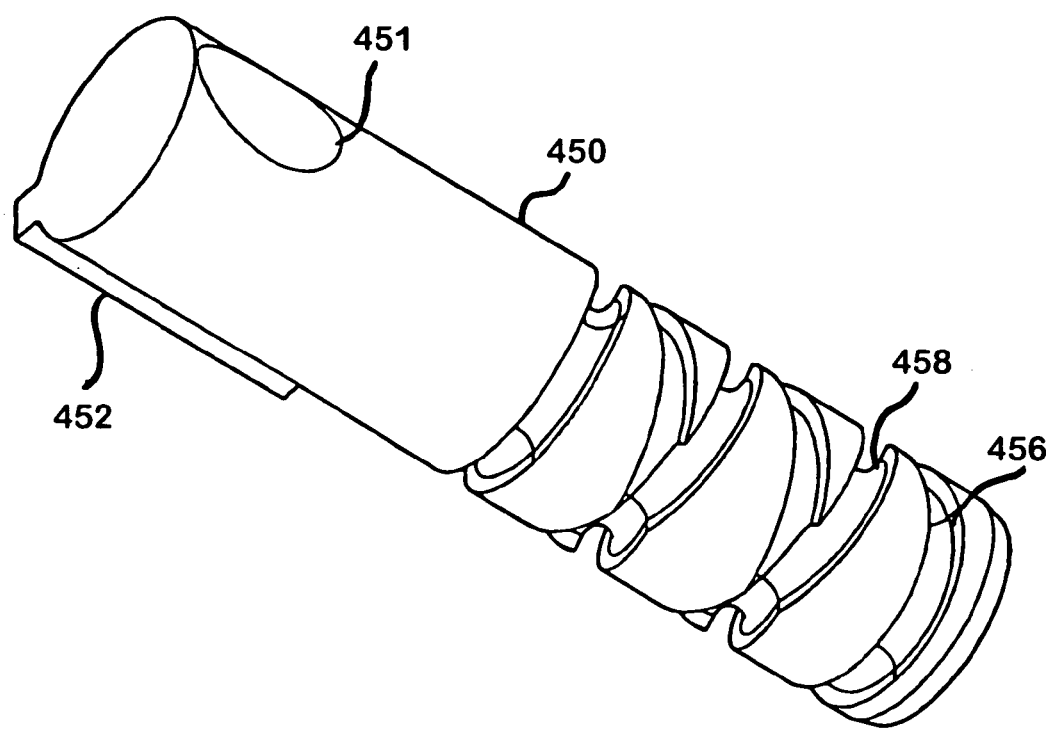
FIG. 15 is a perspective view of the helical member of the surgical instrument of FIG. 12A.

Referring to FIG. 10, the surgeon uses optical devices to guide the surgical instrument 100 through a cavity and towards a targeted tissue 191 of the patient. The surgeon places the surgical instrument 100 against the targeted tissue 191 such that the cutting window 170 exposes the cutting member 185 to the tissue 191. The surgeon activates the rotary driver, which rotates and reciprocates the cutting member 185, as depicted by arrows 192 and 193, respectively. The tissue within the cutting window 170 catches on the hook 174 as the sharp edge 182 of the cutting member 185 slices the tissue as the cutting member 185 rotates and distally advances to cut the tissue. During the time when the sharp edge 182 and the cutting member 185 are advancing distally, debris and fluid from the operative site are sucked by the suction mechanism out of the window 170, through the interior 184 and the lumen 159, and out of the aspiration opening 132. The cut is completed as the sharp edge 182 of the cutting member 185 advances distally beyond the hook 174 of the cutting window 170 within the outer member 186. During the time that the sharp edge 182 of the cutting member 185 has advanced distally beyond the hook 174, the window 170 is closed and no new debris or fluid enters the interior 184 of the cutting member 185 through the window 170. After the cut is completed, the sharp edge 182 retreats proximally from the hook 174 and although the sharp edge 182 is no longer slicing, debris and fluid are aspirated. For most of the time during the reciprocation cycle, fluid is being aspirated because the window 170 is open.

The shape of the cutting window 170 eliminates galling between the inner and outer members 185 and 186, and dulling of the sharp edge 182 of the cutting member 185. Moreover, the sharp edge 182 of the cutting member 185 is axially-disposed so that tissue is grasped by the sharp edge 182 as the sharp edge 182 distally advances to the hook 174.

Figure 11:
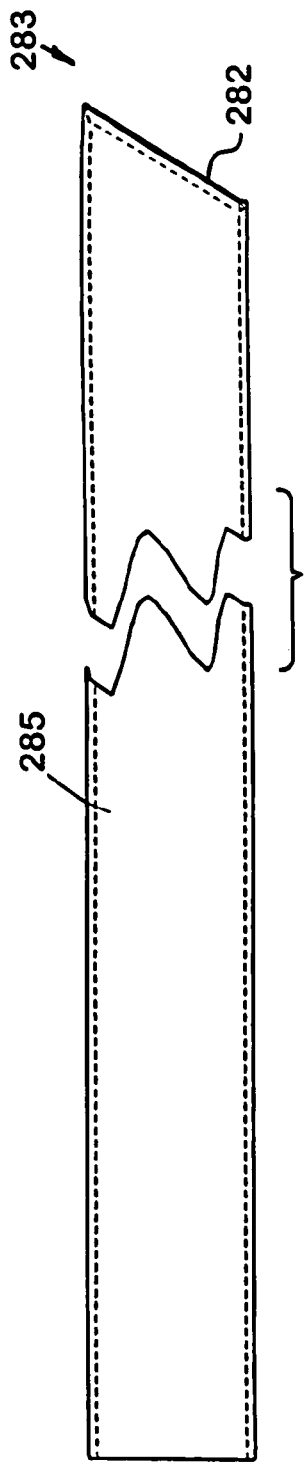
FIG. 11 is a side view of an alternate implementation of the cutting member of a surgical instrument.

Referring to FIG. 11, another implementation of a cutting member 185 is angled at a distal end 283 to a chamfered sharp edge 282 so that the cut in the targeted tissue 191 is initiated on one side and then extends across the width of the tissue. Thus, when the surgical instrument is placed against the targeted tissue 191, rotation and translation of the cutting member 285 and the sharp edge 282 slices the tissue 191.

As discussed above, for most of the time during the reciprocation cycle, fluid is aspirated through the surgical instrument 100 because the window 170 is open for most of the reciprocation cycle. The reciprocating motion of the cutting member 185 and the closing of the window 170 at certain times during the reciprocation cycle creates a pulsing of fluid flow through the surgical instrument 100. This pulsing action can be increased by closing off the fluid path (from the window 170, through the interior 184 and the lumen 159 and out the aspiration opening 132) for a greater period of time during the reciprocation cycle. One way of closing off the fluid path includes adjusting the time and manner with which the lumen 159 and the aspiration opening 132 communicate with each other, as discussed below.

Referring to FIGS. 12A and 12B, in another implementation, a reciprocating rotary surgical instrument 400 is designed with an increased pulsing action by closing off the fluid path for a greater duration during the reciprocation cycle. The surgical instrument 400 includes an inner drive hub 430 having a secondary opening 433 formed to align with an opening 451 of a helical member 450. Other than the inner drive hub 430 and the helical member 450, the instrument 400 is similar in design to the instrument 100 described above. Accordingly, the following discussion relates to the newly-presented features of the inner drive hub 430 and the helical member 450.

Referring also to FIGS. 13A-13D, the inner drive hub 430 includes an aspiration opening 432 having the secondary opening 433 integrally formed distal to the aspiration opening 432. The secondary opening 433 is formed in a cylindrical wall 405 of the inner drive hub 430 and extends into a cylindrical wall 437 of the lumen 436. The secondary opening 433 is formed along a portion of the cylindrical wall 405 that is opposite to a slot 434. The slot 434 has a design and function as detailed above with respect to slot 134. Additionally, the inner drive hub 430 includes a drive coupler 420 that extends from the proximal end of the inner drive hub 430 and mounts in the rotary driver like the drive coupler 120.

Referring to FIGS. 14A-14C and 15, the helical member 450 includes a key 452 and two helical channels 456 and 458 disposed on an outer surface of the helical member 450. The key 452 is shaped like and operates in the same manner as the key 152. Thus, the key 452 mates with the slot 434 of the inner drive hub 430. Furthermore, the helical channels 456 and 458 are shaped like and operate in the same manner as the two helical channels 156 and 158. The helical member 450 includes a lumen 459 extending axially along the helical member 450 and coupling to the opening 451 located at a proximal end of the helical member 450. The opening 451 is oriented at an angle relative to the lumen 459. For example, the opening 451 may be oriented at a 45 degree angle relative to the lumen 459.

Referring also to FIGS. 16A, 16B, 17A, and 17B, in operation, the inner drive hub 430 is mechanically driven by the rotary driver in the same manner as the inner drive hub 130. Additionally, the follower 343 follows the helical channels 456 and 458, as detailed above, to cause the cutting member 185, which is fixed to the helical member 450, to rotate and reciprocate.

Figure 16A:
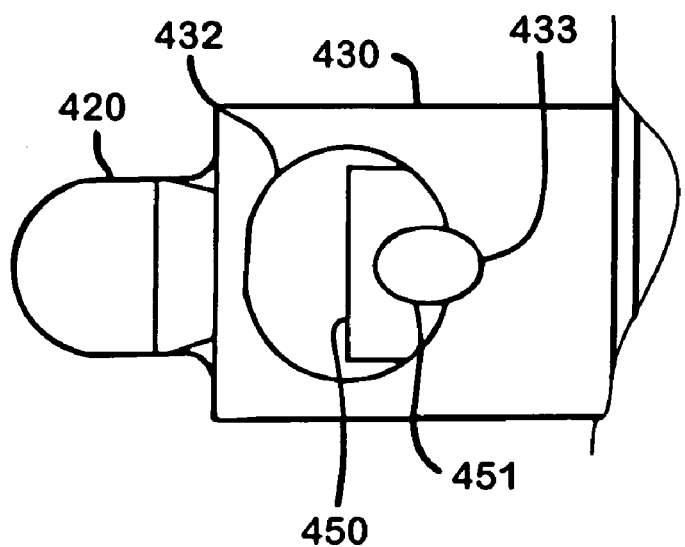
FIGS. 16A and 16B are enlarged side views of a proximal portion of the surgical instrument of FIG. 12A in which the helical member, respectively, protrudes into or clears an aspiration opening of the inner drive hub.
Figure 16B:
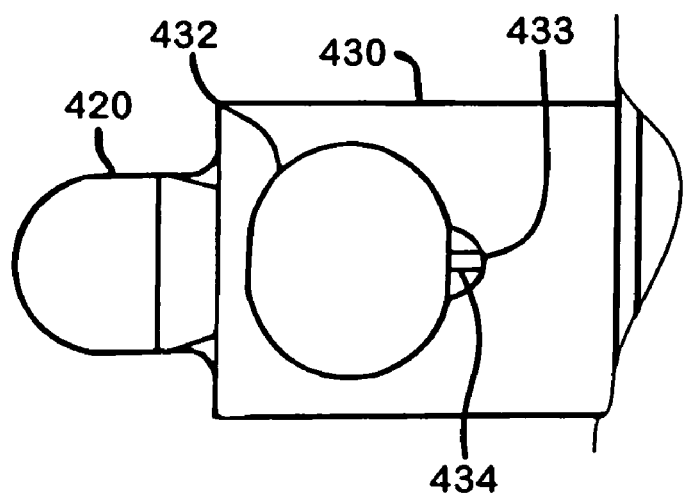
Figure 17A:
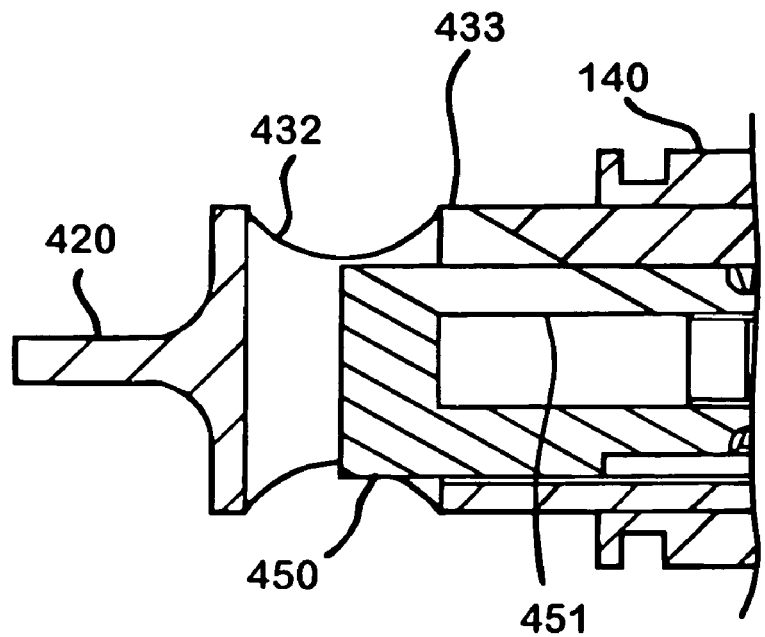
FIGS. 17A and 17B are enlarged cross sectional views of the proximal portion of the surgical instrument of FIG. 12A in which the helical member, respectively, protrudes into or clears the aspiration opening of the inner drive hub.
Figure 17B:
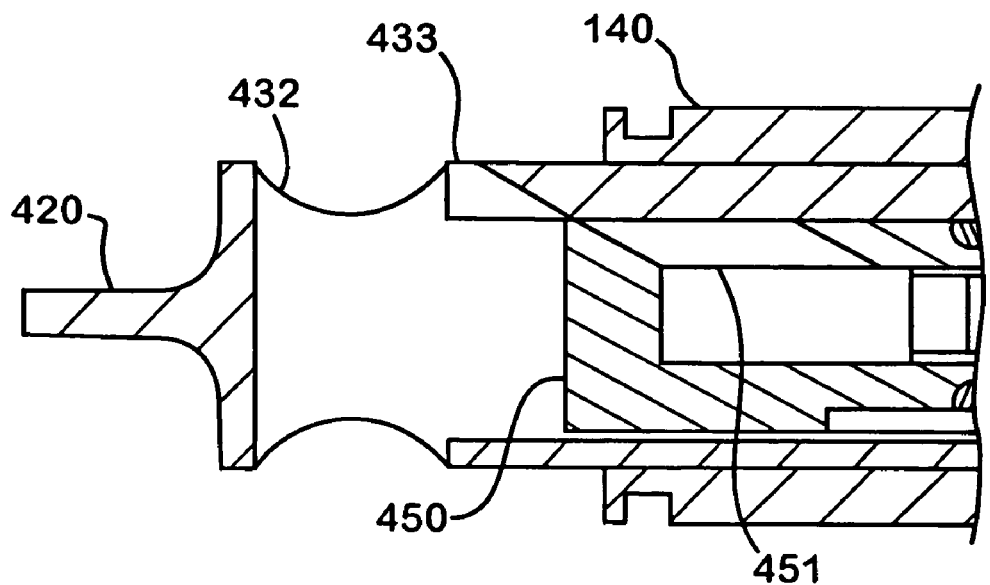
Figure 20:
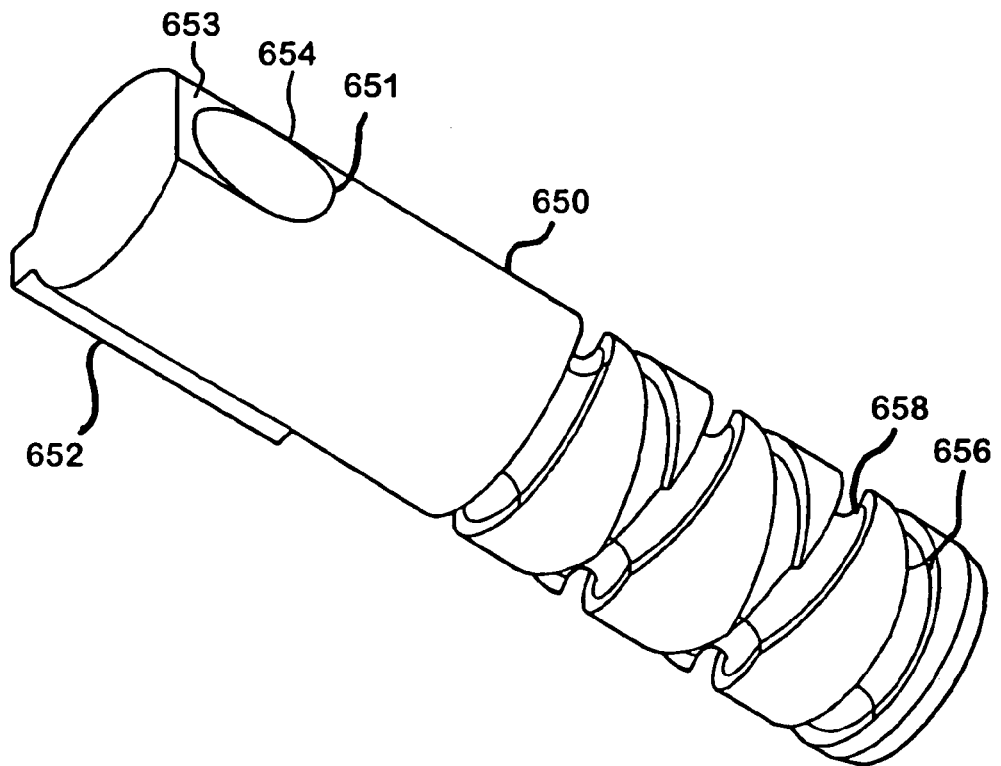
FIG. 20 is a perspective view of the helical member of the surgical instrument of FIG. 12A.

As shown in FIGS. 16A and 17A, a portion of the helical member 450 protrudes into the aspiration opening 432 when the sharp edge 182 of the cutting member 185 retreats from and completely exposes the cutting window 170. This time in the reciprocation cycle may be referred to as a fully open window moment. During the fully open window moment, the opening 433 and the opening 451 align to permit fluid to be sucked through the lumen 459 and the opening 433 by the suction mechanism. Thus, during the fully open window moment, the opening 451 is in complete communication with the aspiration opening 432. Alternately, as shown in FIGS. 16B and 17B, the portion of the helical member 450 previously protruding into the aspiration opening 432 has now cleared the aspiration opening 432 when the sharp edge 182 of the cutting member 185 advances to the hook 174 of the cutting window 170. This time in the cycle may be referred to as a closed window moment. During the closed window moment, the opening 433 and the opening 451 do not align, the opening 451 is in communication with the cylindrical wall 437 of the inner hub 430, and therefore fluid is prevented from flowing through the opening 433 or the aspiration opening 432. The reciprocation cycle extends from the closed window moment to the fully open window moment and back to the closed window moment. At times during the reciprocation cycle other than the fully open or closed window moments, fluid flow is reduced or restricted depending on the location of the opening 433 relative to the opening 451 and the aspiration opening 432.

Fluid from the body cavity is aspirated through the hollow interior 184 of the cutting member 185; through the lumen 459 of the helical member 450; and, during the fully open window moment, through the openings 451 and 433 and out of the aspiration opening 432. In particular, when the openings 433 and 451 move into alignment during the fully open window moment and the opening 451 is in communication with the aspiration opening 432, aspiration pressure, which has been building up during the cycle, releases and results in a pulse of fluid flow from the lumen 459, through the openings 451 and 433, and out of the aspiration opening 432. As the helical member 450 translates, the openings 433 and 451 move out of alignment and flow is restricted until the openings align again.

In contrast, in the instrument 100, debris and fluid are aspirated through the hollow interior 184 of the cutting member, through the lumen 159 of the helical member 450, and out the aspiration opening 132 of the inner drive hub 130 at all times during the reciprocation cycle. Thus, the debris and fluid in the instrument 100 are released by the natural reciprocation of the helical member 150. Though this natural reciprocation produces some amount of pulsing of fluid, the pressure build up during times other than the fully open window moment is reduced because a significant amount of fluid is permitted to flow from the aspiration opening 132.

Referring to FIGS. 18A and 18B, in another implementation, a reciprocating rotary surgical instrument 600 includes the inner drive hub 430 and a helical member 650 received within the inner drive hub 430 and including an opening 651 that aligns with the opening 433 in the inner drive hub 43 and a flattened portion 653 milled on the outer surface of the opening 651. Other than the inner drive hub 430 and the helical member 650, the instrument 600 is similar in design to the instrument 100 described above. Accordingly, the following discussion relates to the newly-presented features of the helical member 650 (the newly-presented features of the inner drive hub 430 are discussed above).

Referring to FIGS. 19A-19C and 20, the helical member 650 includes a key 652 and two helical channels 656 and 658 disposed on an outer surface of the helical member 650. The key 652 is shaped like and operates in the same manner as the key 152. Thus, the key 652 mates with the slot 434 of the inner drive hub 430. Furthermore, the helical channels 656 and 658 are shaped like and operate in the same manner as the two helical channels 156 and 158. The helical member 650 includes a lumen 659 extending axially along the helical member 650 and coupling to the opening 651 located at a proximal end of the helical member 650. The opening 651 is oriented at an angle relative to the lumen 659. For example, the opening 651 may be oriented at a 45 degree angle relative to the lumen 659.

Additionally, the helical member 650 includes the flattened portion 653 extending from a graded or stepped portion 654. The flattened portion 653 is milled into an outer surface of the helical member 650 through which the opening 651 extends. The flattened portion 653 is formed from a shaving having a depth D sufficiently sized to enable leakage of fluid out of the opening 433 to dampen the fluid pulses during the fully open window moment. For example, the depth D may be approximately 0.02 inches from the outer surface (shown in FIG. 19C).

Figure 21:
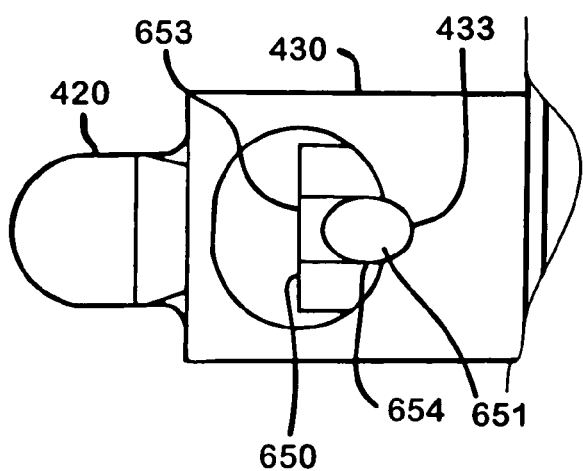
FIG. 21 is an enlarged side view of a proximal portion of the surgical instrument of FIG. 18A in which the helical member protrudes into an aspiration opening of the inner drive hub.
Figure 22A:
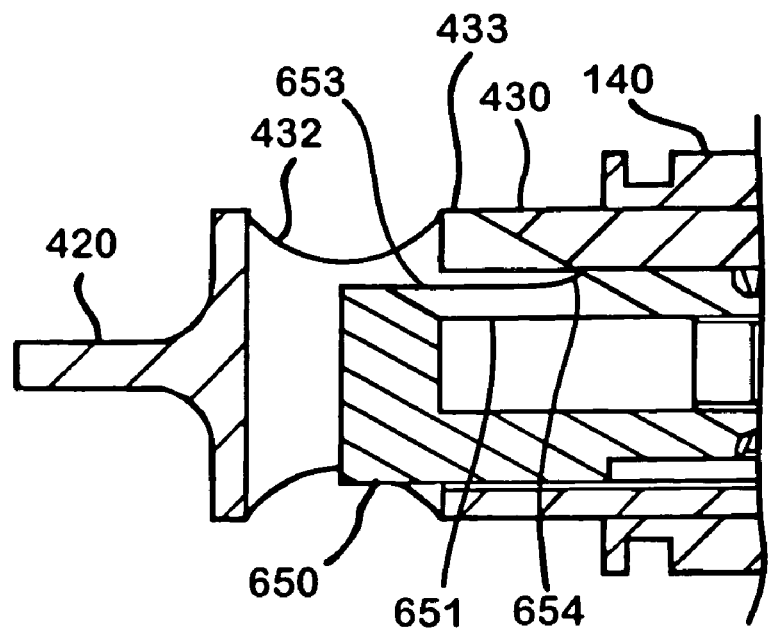
FIGS. 22A and 22B are enlarged cross sectional views of the proximal portion of the surgical instrument of FIG. 18A in which the helical member, respectively, protrudes into or clears the aspiration opening of the inner drive hub.
Figure 22B:
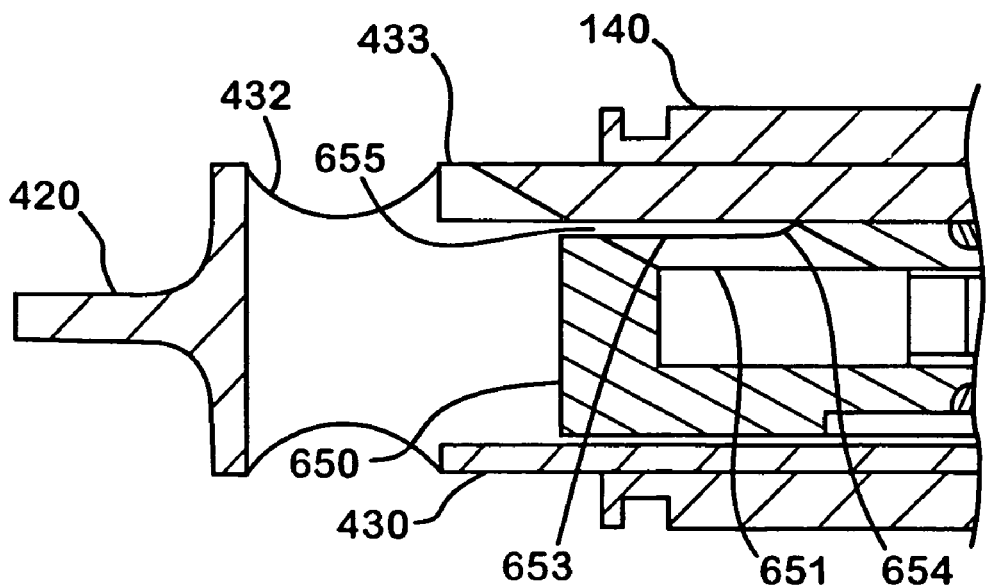

Referring also to FIGS. 21, 22A, and 22B and again to FIG. 16B, in operation, the surgical instrument 600 simultaneously reciprocates and translates the cutting member 185 because the cutting member 185 is fixed to the helical member 650, which is driven by the rotary drive to simultaneously rotate about its axis and reciprocate. For example, as shown in FIGS. 21 and 22A, a portion of the helical member 650 protrudes into the aspiration opening 432 when the sharp edge 182 of the cutting member 185 retreats from and exposes the cutting window 170 (the fully open window moment). During the fully open window moment, the opening 433 and the opening 651 align to permit fluid to flow through the lumen 659 and the opening 433. Alternately, as shown in FIGS. 16B and 22B, the portion of the helical member 650 previously protruding into the aspiration opening 432 has now cleared the aspiration opening 432 when the sharp edge 182 of the cutting member 185 advances to the hook 174 of the cutting window 170 (the closed window moment).

Fluid from the body cavity is aspirated through the hollow interior 184 of the cutting member 185; through the lumen 659 of the helical member 650; and, during the fully open window moment, out of the openings 651 and 433. In particular, when the openings 433 and 651 move into alignment during the fully open window moment, aspiration pressure, which has been building up during the cycle, releases and results in a pulse of fluid flow from the lumen 659 and through the openings 651 and 433. As the helical member 650 reciprocates and translates, the openings 433 and 651 move out of alignment and flow is reduced until the openings align again. During the closed window moment, the opening 433 and the opening 651 do not align. However, the flattened portion 653 provides an opening 655 during the closed window moment that permits a small portion of fluid to still flow (or leak) out of the opening 433. This fluid flow during the closed window moment, although minimal, dampens the fluid pulses and allows for more accurate pressure modulation in the operative cavity at other times including the fully open window moment.

In contrast with the instrument 400, though the instrument 600 provides a significant build up of fluid pressure, the fluid pressure is slightly dampened due to the leak out of the opening 433 at times other than the fully open window moment. This dampening ensures more accurate pressure modulation and control of the body cavity.

A number of implementations have been described. Nevertheless, it will be understood that various modifications may be made. For example, instead of a double helical channel, the helical member may include a single helical channel with a retractable follower and a spring, or possibly, attracting and repelling forces of magnets or a solenoid could enable the rotating and reciprocating movements. Also, alternatively, the inner and outer members may have a cross-sectional shape other than circular. Additionally, the shape of the hook of the outer member may be modified in order to improve grasping of the tissue or grasping a larger volume of tissue. Accordingly, other implementations are within the scope of the following claims.

In another implementation, pulsing action can be improved using a surgical instrument having the inner drive hub 130 (which is designed solely with the aspiration opening 132 in FIG. 1A) and the helical member 450 (which includes the opening 451). The opening 451 communicates with the aspiration opening 132 when the helical member 450 advances into the aspiration opening 132 and the opening 451 communicates with the cylindrical wall of the inner hub 130 when retreating distally into the lumen of the inner hub 130, thus blocking the fluid path from the window 170.

In other implementations, the aspiration opening may be of any suitable shape to enable aspiration of the fluid and debris out of the surgical instrument. Thus, the aspiration opening may be circular, polygonal, or asymmetrical. The opening in the helical member 450 may be at any suitable location along the side or proximal end of the helical member 450.

The location and/or the size of the opening in the helical member may be adjusted depending on the environment and use of the surgical instrument. For example, the helical member may be designed with a pivotable flap that lies flush with the outer surface of the helical member and that pivots about an axis when the flap has advanced into the aspiration opening 132 and beyond the inner drive hub 130. As the helical member distally retracts and the flap is pulled out of the aspiration opening, the edge of the inner hub 130 engages the flap and closes the flap. Such as design would enable a wider adjustment of times when the fluid flow path is blocked because the flap can be configured to close and block fluid flow for varying amounts of time. The flap may permit some amount of fluid to flow around its edges when closed.

In any case, the surgical instruments described above enable the surgeon to reduce or control fluid flow or aspiration even when the window 170 is exposed, that is, at times when the sharp edge 182 is not engaging the hook 174.

In the surgical instruments described above, the cutting member 185 rotates and translates relative to the outer member 186. However, the surgical instrument may be designed such that the cutting member 185 rotates relative to the outer member 186 and the outer member 186 translates relative to the cutting member 185. Thus, the cutting window 170 is moved in relation the cutting member 185. In this implementation the inner drive hub 130 and the helical member 150 are formed from one piece, and the helical channel 156 protrudes into the distal end of the outer hub 140. The outer hub 140 is divided into two outer hub sections (a distal outer hub section and a proximal outer hub section) at some point proximal the translation piece 145. The two outer hub sections are engaged with a keyed cylindrical form similar to the key 152 on the helical member 150 detailed above. This design of the outer hub 140 permits axial movement of the distal outer hub section but eliminates rotational movement of the distal outer hub section. The outer member 186 is firmly fixed to the distal outer hub section and reciprocates with the distal outer hub section.

In another implementation, the cutting member 185 may simply reciprocate without rotating.

In a further implementation, the surgical instrument provides both mechanical cutting of tissue and electrical energy (at high or radio frequency) to activate the cutting window 170 and cause coagulation of tissue during surgery. In this implementation, the outer member 186 is made of an outer tube and a middle tube that are attached to the outer hub 140. The outer tube of the outer member 186 includes an outer surface having an insulating coating. The middle tube of the outer member 186 also includes an outer surface that is coated with insulation. Furthermore, the outer tube of the outer member 186 includes a non-insulated distal end that acts as a return electrode. The electrical connection for the return electrode is an uninsulated or conductive section at a proximal end of the outer tube. The inner surface of the middle tube contacts the outer surface of the cutting member 185 to supply high frequency (that is, radio frequency) power to the cutting member 185 such that the distal end of the cutting member 185 acts as an active electrode. The cutting edge of the middle tube is not insulated. The electrical connection for the active electrode is an uninsulated or conductive section at a proximal end of the middle tube.

To provide coagulation simultaneously or intermittently with tissue cutting, the surgical instrument includes an electrical connector that connects the return and active electrical connections to a generator to provide radio frequency energy to the return electrode and the active electrode. The generator may be, for example, a Valleylab Electrosurgical Generator such as the Force™ FX, the Force™ C, or the Force™ 2 or an ORATEC generator such as the Vulcan® EAS® generator available from Smith & Nephew, Inc. By applying radio frequency energy to the surgical instrument, tissue undergoing resection by mechanical cutting action of the cutting member 185 is coagulated.

What is claimed is:

1. A surgical instrument, comprising:
   a cutting member including an implement for cutting tissue and a lumen extending longitudinally from a distal end of the cutting member;
   an outer tubular member that receives the cutting member, the outer tubular member including a cutting window disposed proximate to a tip of the outer tubular member; and
   a drive coupled to the cutting member to simultaneously rotate and translate the cutting member in response to a force applied to the drive;
   wherein the drive comprises:
      an aspiration opening; and
      a restriction mechanism that selectively restricts fluid flow from the lumen of the cutting member to the aspiration opening such that fluid is restricted from flowing out of the surgical instrument for at least some time during operation of the surgical instrument; wherein the selective restriction is caused by the movement of the drive; wherein the restriction mechanism includes:
         at least a section of a drive member attached to the cutting member and having a proximally-positioned opening that communicates with the lumen of the cutting member, and
         an inner drive hub that includes the aspiration opening.

2. The instrument of claim 1, wherein the drive is configured such that the translation of the cutting member comprises reciprocation.

3. The instrument of claim 1, wherein the drive includes a drive member attached to the cutting member, the drive member including a helical groove.

4. The instrument of claim 3, wherein the drive includes a translation piece disposed in the groove such that rotary driving of the drive member results in simultaneous reciprocation of the drive member relative to the translation piece.

5. The instrument of claim 4, wherein the translation piece includes a follower received within the groove and a sealing cap over the follower, with the follower being free to swivel relative to the sealing cap.

6. The instrument of claim 5, wherein the follower has an arched bridge shape.

7. The instrument of claim 4, wherein the translation piece is coupled to the drive member such that the translation piece is disposed in the helical groove and swivels to follow the helical groove as the drive member rotates.

8. The instrument of claim 3, wherein the inner drive hub is coupled to the drive member and defines a slot, and the drive member includes a key received in the slot and rotatably coupling the drive member to the inner drive hub such that the drive member rotates with the inner drive hub while being free to translate relative to the inner drive hub.

9. The instrument of claim 3, wherein the helical groove comprises a left-hand threaded helical channel.

10. The instrument of claim 3, wherein the helical groove comprises a right-hand threaded helical channel.

11. The instrument of claim 3, wherein the helical groove comprises two helical channels, a first helical channel being a left-hand threaded helical channel and a second helical channel being a right-hand threaded helical channel.

12. The instrument of claim 11, wherein the first helical channel and the second helical channel form a continuous path.

13. The instrument of claim 3, wherein the cutting member is attached to the drive member to move rotatably and axially with the drive member.

14. The instrument of claim 1, wherein the implement comprises a chamfered cutting edge at a distal end of the cutting member.

15. The instrument of claim 14, wherein the chamfered edge of the cutting member comprises a straight cutting edge.

16. The instrument of claim 14, wherein the chamfered edge comprises an angled cutting edge.

17. The instrument of claim 1, wherein the cutting window comprises an opening in the outer tubular member exposing the cutting member to tissue.

18. The instrument of claim 17, wherein the cutting window comprises a U-shaped proximal end and a saddle-shaped distal end.

19. The instrument of claim 17, wherein the saddle-shaped distal end of the cutting window includes a hook.

20. The instrument of claim 1, wherein:
the cutting member is slidably received within the outer tubular member such that the lumen is able to communicate with the cutting window.

21. The instrument of claim 20, wherein the restriction mechanism selectively restricts fluid flow from the lumen to the aspiration opening by restricting fluid flow when the lumen communicates with the cutting window.

22. The instrument of claim 1, wherein the cutting member includes an active electrode and a return electrode located at a non-insulated distal end portion of the cutting member.

23. The instrument of claim 22, further comprising an electrical connector that connects to the return and active electrodes of the cutting member and to a generator to provide high frequency energy to the cutting member.

24. The instrument of claim 1, wherein the restriction mechanism is formed from the interaction of the drive member opening and the inner drive hub aspiration opening.

25. The instrument of claim 1, wherein the restriction mechanism reduces the amount of coupling between the proximally-positioned opening of the drive member and the aspiration opening of the inner drive hub.

26. The surgical instrument of claim 1, wherein the restriction mechanism selectively restricts fluid flow from the lumen of the cutting member to the aspiration opening and out of the surgical instrument for at least some time during operation of the surgical instrument.

27. The surgical instrument of claim 1, wherein the restriction mechanism selectively restricts fluid flow from the lumen of the cutting member to the aspiration opening such that fluid is only permitted to flow out of the surgical instrument for at least some time during operation of the surgical instrument.

28. The surgical instrument of claim 1, further comprising a suction mechanism coupled to a proximal end of the drive and to the aspiration opening.

29. A surgical instrument comprising:
a cutting member including an implement for cutting tissue;
an outer tubular member that receives the cutting member, the outer tubular member including a cutting window disposed proximate to a tip of the outer tubular member; and
a drive coupled to the cutting member to simultaneously rotate, reciprocate, and translate the cutting member in response to a continuous force applied at a proximal end of the surgical instrument and to the drive,
wherein the drive includes a drive member attached to the cutting member, the drive member including a helical groove,
wherein the drive member comprises:
an opening formed in an outer circumferential wall of the drive member, and
a lumen for attaching the cutting member.

30. The surgical instrument of claim 29, wherein the drive member opening is oriented at an angle relative to the lumen.

31. The surgical instrument of claim 30, wherein the drive member opening is angled at approximately 45 degrees relative to the lumen of the drive member.

32. The surgical instrument of claim 29, wherein:
the drive includes an inner drive hub coupled to the drive member, and
the inner drive hub includes an opening such that at a predetermined point during simultaneous rotation and translation of the cutting member, the drive member opening and the inner drive hub opening align to permit a fluid pulse through the openings.

33. The surgical instrument of claim 32, wherein the inner drive hub includes an aspiration opening and the inner drive hub opening is formed integral with a distal end of the aspiration opening.

34. The surgical instrument of claim 29, wherein the drive member comprises a flattened portion.

35. The surgical instrument of claim 34, wherein the flattened portion is formed adjacent to the drive member opening.

36. The surgical instrument of claim 35, wherein:
the drive includes an liner drive hub coupled to the drive member and including an opening, and
the flattened portion and the inner drive hub opening define a second opening extending between the drive member opening and the inner drive hub opening.

37. The surgical instrument of claim 29, wherein the drive is coupled to the cutting member to simultaneously rotate and translate the cutting member in response to only a rotational force applied to the drive.

38. The surgical instrument of claim 29, further comprising a suction mechanism coupled to a proximal end of the lumen.

39. A surgical instrument comprising:
a cutting member including an implement for cutting tissue;
an outer tubular member that receives the cutting member, the outer tubular member including a cutting window disposed proximate to a tip of the outer tubular member; and
a drive coupled to the cutting member to simultaneously rotate and translate the cutting member in response to a force applied to the drive,
wherein the drive includes:
a drive member attached to the cutting member and having a helical groove, and an inner drive hub coupled to the drive member and having an opening, wherein the drive member is positioned within the inner drive hub and includes:
  a hollow cylindrical wall extending along a longitudinal axis, defining a lumen that extends along the longitudinal axis from the cutting member at its distal end to a closed proximal end, wherein an opening is formed in the cylindrical wall and in fluid communication with the lumen.

40. The surgical instrument of claim 39, further comprising a suction mechanism coupled to a proximal end of the lumen.

41. A surgical instrument comprising:
  a cutting member including an implement for cutting tissue;
  an outer tubular member that receives the cutting member, the outer tubular member including a cutting window disposed proximate to a tip of the outer tubular member; and
  a drive coupled to the cutting member to simultaneously rotate and translate the cutting member in response to a force applied to the drive, wherein the drive includes:
    a drive member that is attached to the cutting member and includes an opening, and
    an inner drive hub that rotates with the drive member and includes an opening;
  wherein a fluid outflow path including an interior of the cutting member, the drive member opening, and the inner drive hub opening is formed when the drive member opening aligns with the inner drive hub opening, and
  wherein fluid is restricted from flowing out of the surgical instrument at least during a moment when the drive member opening is not aligned with the inner drive hub opening.

42. The surgical instrument of claim 41, further comprising a suction mechanism coupled to a proximal end of the fluid outflow path.

43. The surgical instrument of claim 41, wherein fluid is able to flow out of the surgical instrument at least during the moment when the drive member opening is aligned with the inner drive hub opening.

44. A surgical instrument comprising:
  a cutting member including an implement for cutting tissue and a lumen extending longitudinally from a distal end of the cutting member;
  an outer tubular member that receives the cutting member, the outer tubular member including a cutting window disposed proximate to a tin of the outer tubular member; and
  a drive coupled to the cutting member to simultaneously rotate and translate the cutting member in response to a force applied to the drive;
  wherein the drive comprises:
    an aspiration opening; and
    a restriction mechanism that selectively restricts fluid flow from the lumen of the cutting member to the aspiration opening such that fluid is flowing out of the surgical instrument for at least some time during operation of the surgical instrument; wherein the selective restriction is caused by the movement of the drive, and
  wherein the drive is coupled to the cutting member to simultaneously rotate and translate the cutting member in response to only a rotational force applied to the drive.

45. The surgical instrument of claim 44, further comprising a suction mechanism coupled to a proximal end of the drive and to the aspiration opening.

46. The surgical instrument of claim 44, wherein the restriction mechanism selectively restricts fluid flow from the lumen of the cutting member to the aspiration opening and out of the surgical instrument for at least some time during operation of the surgical instrument.

47. The surgical instrument of claim 44, wherein the restriction mechanism selectively restricts fluid flow from the lumen of the cutting member to the aspiration opening such that fluid is only permitted to flow out of the surgical instrument for at least some time during operation of the surgical instrument.

48. A surgical instrument comprising:
  a cutting member including an implement for cutting tissue;
  an outer tubular member that receives the cutting member, the outer tubular member including a cutting window disposed proximate to a tip of the outer tubular member; and
  a drive coupled to the cutting member to simultaneously rotate and translate the cutting member in response to a force applied to the drive,
  wherein the drive includes a drive member attached to the cutting member, the drive member including a helical groove,
  wherein the drive member comprises:
    an opening formed in an outer circumferential wall of the drive member, and
    a lumen for attaching the cutting member.

* * * * *